United States Patent
Capriotti et al.

(10) Patent No.: US 9,750,683 B2
(45) Date of Patent: *Sep. 5, 2017

(54) ANTIFUNGAL COMPOSITIONS FOR THE TREATMENT OF SKIN AND NAILS

(71) Applicants: Joseph Capriotti, Christiansted, VI (US); Kara Capriotti, Fort Washington, PA (US); Stuart Lessin, Haverford, PA (US)

(72) Inventors: Joseph Capriotti, Christiansted, VI (US); Kara Capriotti, Fort Washington, PA (US); Stuart Lessin, Haverford, PA (US)

(73) Assignee: Veloce BioPharma, LLC, Fort Lauderdale, FL (US)

( * ) Notice: Subject to any disclaimer, the term of this patent is extended or adjusted under 35 U.S.C. 154(b) by 79 days.

This patent is subject to a terminal disclaimer.

(21) Appl. No.: 14/378,937

(22) PCT Filed: Nov. 15, 2012

(86) PCT No.: PCT/US2012/065298
§ 371 (c)(1),
(2) Date: Aug. 14, 2014

(87) PCT Pub. No.: WO2013/122637
PCT Pub. Date: Aug. 22, 2013

(65) Prior Publication Data
US 2015/0335676 A1    Nov. 26, 2015

Related U.S. Application Data

(60) Provisional application No. 61/600,268, filed on Feb. 17, 2012.

(30) Foreign Application Priority Data

May 8, 2012    (WO) ................ PCT/US2012/036942

(51) Int. Cl.
| | | |
|---|---|---|
| *A61K 31/79* | (2006.01) | |
| *A61K 9/00* | (2006.01) | |
| *A61K 47/20* | (2006.01) | |
| *A61K 45/06* | (2006.01) | |
| *A61K 33/18* | (2006.01) | |
| *A61K 9/08* | (2006.01) | |

(52) U.S. Cl.
CPC .......... *A61K 9/0012* (2013.01); *A61K 9/0014* (2013.01); *A61K 31/79* (2013.01); *A61K 33/18* (2013.01); *A61K 45/06* (2013.01); *A61K 47/20* (2013.01); *A61K 9/08* (2013.01)

(58) Field of Classification Search
CPC ................................................ A61K 2300/00
See application file for complete search history.

(56) References Cited

U.S. PATENT DOCUMENTS

| | | | |
|---|---|---|---|
| 3,551,554 A * | 12/1970 | Herschler ............ | A61K 9/0014 424/184.1 |
| 4,652,557 A | 3/1987 | Sandborn | |
| 6,391,879 B1 | 5/2002 | Reeves | |
| 2005/0123625 A1* | 6/2005 | Burke .................. | A61K 9/0014 424/667 |
| 2006/0165747 A1 | 7/2006 | Rolf | |
| 2009/0162301 A1 | 6/2009 | Tarrand | |
| 2010/0029781 A1* | 2/2010 | Morris ................. | A61K 9/0048 514/646 |

FOREIGN PATENT DOCUMENTS

| | | | |
|---|---|---|---|
| GB | 2275191 A | | 8/1994 |
| WO | WO/2012/154740 | * | 11/2012 |
| WO | WO 2012/154740 A1 | | 11/2012 |

OTHER PUBLICATIONS

Ourhealth (Ourhealth.com Discussions by Condition: Skin Conditions—Molluscum Contagiosum Discussion—posted online Sep. 2009).*
Berkelman, Ruth, et al., Journal of Clinical Microbiology, Apr. 1982, p. 635-639 vol. 15, No. 4.
International Search Report in PCT/US2012/036942.
International Search Report in PCT/US2014/025470.
International Search Report and IPRP/Written Opinion in PCT/US2012/065298.
K. Capriotti, et al., A Novel Topical 2% Povidone-Iodine Solution for the Treatment of Common Warts: A Randomized, Double-blind, Vehicle-Controlled Trial, Dermatol Ther., Nov. 3, 2015 (DOI 10.1007/s13555-015-0086-1) (open access at Springerlink.com).
K. Capriotti, et al., Molluscum Contagiosum Viral Infention Treated With a Dilute Povidone-Iodine/Dimethylsulfoxide Prepartion, Derm Ther. Dec. 21, 2015 (DOI 10.1007/s13555-015-0091-4) (open access at Springerlink.com).
K. Capriotti, et al., Molluscum Contagiosum Treated With Dilute Povidone-Iodine: A Series of Cases, JCAD (accepted for publication) 2016.
Stulberg, DL and Hutchinson, AG, Molluscum Contagiosum and Warts. Am. Fam .Physician. Mar. 15, 2003; 67 (6):pp. 1233-1240.
Van Der Wouden, JC, et al. Interventions for cutaneous molluscum contagiosum. Cochrane Database Syst. Rev. Apr. 19, 2006;(2):CD004767.
Capriotti, K., et al., Molluscum Contagiosum Treated With Dilute Povidone-Iodine: A Series of Cases. J. Clin. Aesthet. Derm. (2016) (in press).

* cited by examiner

*Primary Examiner* — David J Blanchard
*Assistant Examiner* — Sarah Alawadi
(74) *Attorney, Agent, or Firm* — Ted Whitlock

(57) ABSTRACT

Disclosed herein are antifungal compositions for treatment of skin and nails, as well as methods of making and using the same.

1 Claim, No Drawings

ANTIFUNGAL COMPOSITIONS FOR THE TREATMENT OF SKIN AND NAILS

CROSS-REFERENCE TO RELATED APPLICATIONS

This application is a 371 filing from PCT/US2012/065298, filed Nov. 15, 2012, which claims the benefit of U.S. Provisional Application, Ser. No. 61/600,268, filed Feb. 17, 2012.

BACKGROUND

Skin diseases and conditions, such as acne, dermatitis, and rosacea, can be further complicated by way of microbial colonization and/or infection. For example, acne, a well known and common skin disease, has very different forms as well as grades of severity, from simple acne vulgaris, extending to the more dangerous forms such as acne conglobate, which can lead to severe disfigurements of the skin. Disregarding it, as well as excessive and improper treatment, can lead to irreversible scars and changes of the skin, and consequent adverse effects to quality of life. To a large extent, the aforementioned is also true for seborrheic dermatitis and other skin diseases in their different forms such as herpes, from simple irritations of the skin up to severe and irreversible changes of epidermis.

Traditionally, there were basically two possibilities for the therapy of acne, seborrheic dermatitis and other related skin diseases: Topical (exterior) treatment and oral treatment which is effective via the metabolism. The oral treatment, for example, is principally used only for very severe forms of acne, since retinoids and related active agents may have very strong side effects. Even the topical remedies traditionally used were of questionable safety when applied at the concentration necessary for the desired therapeutic effect. Antibiotic preparations, mainly used for fighting secondary infections, are generally subject to prescription. In addition, benzoyl peroxide, which is the topical remedy most used, is by no means as harmless as it would be desirable for at least the treatment of young people. In addition to its suspected carcinogenic effect established in tests with animals, it is very aggressive, and its main effect consists of the oxidation of the upper skin layers like a chemical scalpel, thereby chemically isolating these layers and causing irritation. The same applies for salicylic acid which is used to dissolve the skin by its keratolytic effect.

Onychomycosis—nail fungal infection—affects 30-60 million patients each year in the United States. It is the most common disease of the nails and constitutes about a half of all nail abnormalities. This condition may affect toenails or fingernails, but toenail infections are particularly common. The prevalence of onychomycosis is about 6-8% of the United States adult population. Common signs of onychomycosis include a thickened, yellow, or cloudy appearance of the nails. The nails can become rough and crumbly, and can separate from the nail bed. Patients with onychomycosis may experience significant psychosocial problems due to the appearance of the nail.

The causative pathogens of onychomycosis include dermatophytes, *Candida*, and nondermatophytic molds. Dermatophytes are the fungi most commonly responsible for onychomycosis in the temperate western countries, while *Candida* and nondermatophytic molds are more frequently involved in the tropics and subtropics with a hot and humid climate. *Trichophyton rubrum* is a common dermatophyte involved in onychomycosis. Other dermatophytes that may be involved are *T. mentagrophytes, Epidermophyton floccosum, T. violaceum, Microsporum gypseum, T. tonsurans, T. soudanense* and the cattle ringworm fungus *T. verrucosum*. Other causative pathogens include *Candida* and nondermatophytic molds, in particular members of the mold generation *Scytalidium* (now called Neoscytalidium), Scopulariopsis, and *Aspergillus. Candida* spp. are known to cause fingernail onychomycosis in people whose hands are often submerged in water. *Scytalidium* mainly affects people in the tropics, though it persists if they later move to areas of temperate climate. Control of these pathogens can be used to treat onychomycosis.

BRIEF SUMMARY

In an embodiment, disclosed herein is a composition for treating a skin disease and/or condition. Skin diseases include Molluscum contagiousum, seborrheic dermatitis, hand hermatitis, atopic dermatitis, acne, rosacea, and Verruca vulgaris. In an embodiment, disclosed herein is a composition for treating a skin disease and/or condition complicated by microbial colonization and/or infection.

In an embodiment, disclosed herein is a composition for treating a skin disease complicated by microbial colonization and/or infection, the composition comprising an iodophor and dimethylsulfoxide (DMSO), wherein the composition is capable of penetrating the skin to treat the infection. In an embodiment, the composition can treat the skin disease by penetrating the skin. In an embodiment, the composition can treat the skin disease without penetrating the skin. In an embodiment, the composition can treat the skin disease prior to penetrating the skin. In an embodiment, the composition can treat the skin disease both by penetrating the skin and prior to penetrating the skin.

In an embodiment, disclosed herein is a composition for treating a skin disease complicated by microbial colonization and/or infection, the composition comprising elemental iodine and dimethylsulfoxide (DMSO), wherein the composition is capable of penetrating the skin to treat the infection. In an embodiment, the iodophor is selected from the group consisting of povidone iodine (PVP-I), iodine tincture, Lugol's solution, potassium iodide, and sodium iodide.

In an embodiment, a composition disclosed herein for treatment of a skin disease complicated by microbial colonization and/or infection is substantially anhydrous. In an embodiment, the composition is anhydrous.

In an embodiment, a composition disclosed herein for treatment of a skin disease complicated by microbial colonization and/or infection includes PVP-I at about 0.01% to about 10% (w/w). In an embodiment, PVP-I is present in a range selected from the group consisting of about 0.05% to about 10%, about 0.1% to about 5%, about 0.2% to about 2.5%, and about 0.5% to about 1% (w/w). In an embodiment, PVP-I is present in a range selected from the group consisting of about 0.1%, about 0.2%, about 0.3%, about 0.4%, about 0.5%, about 1.0%, about 1.25%, about 1.5%, about 2.0%, about 2.5%, and about 5% (w/w). In an embodiment, PVP-I is present at about 1% (w/w).

In an embodiment, a composition disclosed herein for treatment of a skin disease complicated by microbial colonization and/or infection further comprises at least one naturopathic substance. In an embodiment, a composition disclosed herein for treatment of a skin disease complicated by microbial colonization and/or infection further comprises at least one substance selected from the group consisting of *Punica Granatum* Extract, *Camellia Sinensis* Leaf Extract, Ascorbic Acid, *Calendula Officinalis*, Extract, *Glycrrhiza Glabra* Extract, Allantoin, and *Cucumis Sativus* Fruit Extract.

In an embodiment, a composition disclosed herein for treatment of a skin disease complicated by microbial colonization and/or infection further comprises at least one antifungal agent selected from the group consisting of tolnaftate, terbinafine, undecylenic acid, clioquinol, miconazole, miconazole nitrate, clorrinazolc, tioconazolc, nystatin, terconazoic, butoconazole nitrate, ciclopirox olamine, econazole nitrate, triacetin, flucytosine, haloprogin, and ketoconazole. In an embodiment, an antifungal agent is present in an amount of about 1% to about 25% (w/w).

In an embodiment, disclosed herein is a composition for treating a skin disease complicated by microbial colonization and/or infection, the composition comprising an iodophor and dimethylsulfoxide (DMSO), wherein the composition is capable of penetrating the skin to treat the infection, further wherein the composition does not comprise a polyglycol.

In an embodiment, disclosed herein is a composition for treating a skin disease complicated by microbial colonization and/or infection, the composition comprising an iodophor and dimethylsulfoxide (DMSO), wherein the pharmaceutical composition is capable of penetrating the skin to treat the infection.

In an embodiment, the infection treated is a fungal infection. In an embodiment, the infection is a dermatophyte infection. In an embodiment, the infection is a bacterial infection.

In an embodiment, disclosed herein is a method for treating a skin disease complicated by microbial colonization and/or infection, comprising contacting an affected area of the skin with a composition disclosed herein and repeating the contacting step as necessary until the skin disease has been treated. In an embodiment, the contacting step is conducted at least once a day. In an embodiment, the skin disease is dermatitis. In an embodiment, the skin disease is rosacea. In an embodiment, the skin disease is acne. In an embodiment, the skin disease is Molluscum contagiousum. In an embodiment, the skin disease is Verruca vulgaris.

In an embodiment, disclosed herein is a method of treating a skin disease complicated by microbial colonization and/or infection, comprising contacting an affected area of the skin with a composition disclosed herein and repeating the contacting step for at least four weeks.

DETAILED DESCRIPTION

Povidone-iodine (PVP-I) is a well known antiseptic to almost every medical specialty. It has gained recent interest beyond simple disinfection as a therapy for active infections in the eye, ear, sinuses, articular compartments and skin. There is no known antibiotic, fungal or viral resistance to PVP-I and no known species of yeast or fungus that cannot be eliminated with PVP-I. The development of resistance, which is inevitable for certain species when using most conventional antibiotics, is extremely unlikely given the mechanism of PVP-I antisepsis. PVP-I has also been shown to inhibit the formation of biofilms and to eliminate biofilms that have already formed.

A variety of organic solvents are known to enhance the percutaneous absorption of medicaments, including dimethylsulfoxide (DMSO). The superiority of DMSO to other solvents both in enhancing penetration and in favoring dermal retention was demonstrated in a study of the passage of $^{14}$C-labelled griseofulvin, dissolved in DMSO, dimethylacetamide, dimethylformamide, alcohol or benzene, through human skin in vitro. The ratios of penetration of griseofulvin in the various solvents was 60, 40, 7, 3, and 1, respectively. Even when a 50% solution of DMSO in water was used, the rate of penetration of $^{14}$C hydrocortisone was markedly enhanced. It has now been surprisingly discovered, as disclosed herein, that DMSO is effective at enhancing penetration into and through the heavily keratinized nail bed.

DMSO has been shown to enhance the percutaneous penetration of many drugs. DMSO has also been shown to enhance the rate of penetration of water through the skin when the epidermis was treated for 30 minutes with 60%, 80% and 90% aqueous solutions of DMSO. Many theories concerning the mechanism of action of penetrants have appeared in the literature. One attributes the penetrant effects of DMSO, dimethylformamide, and dimethylacetamide to their hygroscopic properties which increase the water content of the stratum corneum, thereby greatly increasing its permeability. Another attributes the effectiveness of penetration enhancers to their ability to lower the barrier properties of the stratum corneum by modifying its natural structure. Organic solvents like benzene, alcohol, and ether, which have been shown to enhance the penetration rate of both water soluble and lipid-soluble substances, may act by removing the lipids from the stratum corneum. However, the action of hydrogen-bonding solvents like DMSO, dimethylformamide, and dimethylacetamide, for example, is attributed to membrane expansion and uniform increase in media diffusivity.

In an aspect, as further described herein, it was surprisingly found that anhydrous compositions comprising PVP-I and DMSO are effective for treating ungual fungal infections. This is surprising, in part, because the chemistry of PVP-I has heretofore been taught to require aqueous equilibrium. In an embodiment, it is now shown that aprotic anhydrous compositions comprising PVP-I and DMSO can behave antiseptically in a very similar fashion to aqueous PVP-I compositions. In another aspect, as further described herein, it was surprisingly found that substantially anhydrous compositions comprising PVP-I and DMSO, as well as compositions comprising PVP-I and DMSO comprising less than 10% water (w/w), are effective for treating ungual fungal infections.

In another aspect, as further described herein, is was surprisingly found that the compositions and methods encompassed herein are useful for treating conditions in addition to ungual fungal infections, including, but not limited to, other fungal infections, yeast infections, viral infections, and bacterial infections, including both gram positive and gram negative bacteria. In an aspect, as further described herein, it was surprisingly found that the compositions and methods encompassed herein are useful for treating paronychia. In an aspect, the compositions and methods encompassed herein are useful for treating skin diseases complicated by microbial colonization and/or infection.

Contemplated herein are compositions comprising at least one penetrant and at least one active agent for the treatment of ungual fungal infections, and methods of using the same. Also contemplated herein are compositions comprising at least one penetrant and at least one active agent for the treatment of skin diseases complicated by microbial colonization and/or infection. In an embodiment, disclosed herein are compositions comprising DMSO and PVP-I. Also disclosed herein are methods of using compositions comprising DMSO and PVP-I.

Therapeutic Indications

In an embodiment, disclosed herein are compositions and methods for treating skin diseases complicated by microbial colonization and/or infection. Examples of such conditions and/or diseases include, but are not limited to, Molluscum contagiousum, seborrheic dermatitis, hand dermatitis, atopic dermatitis, acne, rosacea, and Verruca vulgaris. In an embodiment, the composition is used to treat the skin disease by penetrating the skin. In an embodiment, the composition is used to treat the skin disease without penetrating the skin. In an embodiment, the composition is used to treat the skin disease prior to penetrating the skin. In an embodiment, the composition is used to treat the skin disease both by penetrating the skin and prior to penetrating the skin.

In an embodiment, disclosed herein are compositions and methods for treating onychomycosis, or nail (ungual) fungal infection. Therefore, the compositions and methods are useful for treatment of the *unguis*, or ungual surfaces, areas adjacent to or contact the *unguis*, or areas nearby an ungual surface. In an embodiment, the compositions and methods herein treat infections located in one or more of the *unguis*, the subungual space, and the periungual space. The compositions and methods are further useful in treating any combination of the above.

The term "treating", as used herein, refers to a detectable improvement in an adverse condition and/or a lessening the symptoms of the condition upon contacting a mammal with a composition disclosed or encompassed by the disclosure herein. The term "treating" encompasses both a partial improvement in an adverse condition and a complete eradication (i.e., "cure") of the condition. In an aspect, an infection is treated.

As the term is used herein, an "affected" area of the skin is an area of the skin involved in the disease state or adverse condition. By way of a non-limiting example, an affected area of the skin in a case of hand dermatitis includes skin on, around, or near the hand that demonstrates one or more signs, symptoms, characteristics, or properties of a dermatitis condition as would be understood by the skilled artisan.

The compositions and methods are useful for treatment of infections involving, but not limited to, dermatophytes, *Candida*, and nondermatophytic molds. The compositions and methods are useful for treating infections involving *Trichophyton rubrum, T. mentagrophytes, Epidermophyton floccosum, T. violaceum, Microsporum gypseum, T. tonsurans, T. soudanense, T. verrucosum*, as well as *Neoscytalidium, Scopulariopsis*, and *Aspergillus*.

The compositions can also be used to treat virtually any kind of fungal and/or mycotic pathogens (some of which are described in Scrip's Antifungal Report (1992)) responsible for a variety of diseases in humans, ranging from mycoses involving *unguis*, skin, hair, or mucous membranes, further including, but not limited to, *Absidia* spp., *Actinomadura madurae, Actinomyces* spp., *Alleschenia boydii, Alternaria* spp., *Anthopsis deltoidea, Apophysomyces elegans, Arnium leoporinum, Aspergillus* spp., *Aureobasidiun pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora accrina, Nocardia* spp., *Paracoccidioidcs brasilicnsis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces phaeomuriformis, Sporothrix schenckii, Syncephalastirum racemosuin, Taeniolella boppii, Torulopsosis* spp., *Trichophyton* spp., *Trichosporon* spp., *Ulocladium chartarum, Wangiella dermatitidis, Xylohypha* spp., *Zygomyetes* spp., *Tinea barbae, Tinea capitis, Tinea corporis, Tinea cruris, Tinea favosa, Tinea imbricata, Tinea manuum, Tinea nigra* (*palmalis*), *Tinea pedis, Tinea unguium, Torulopsosis, Trichomycosis axillaris, White piedra*. Such organisms are responsible for conditions and infections such as, but not limited to *Otitis externa* (otomycosis), *Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis*, North American *Blastomycosis, Paracoccidioidomycosis, Phaeohyphomycosis, Phycomycosis*, pneumocystic pneumonia, *Pythiosis, Sporotrichosis*, and *Torulopsosis*. Other fungi that have pathogenic potential include, but are not limited to, *Thermomucor indicae-seudaticae, Radiomyces* spp., and other species of known pathogenic genera. These fungal organisms are ubiquitous in air, soil, food, decaying food, etc.

The compositions and methods encompassed herein may also have anti-viral and/or anti-bacterial properties. In an embodiment, treatment of a patient using the compositions and methods encompassed herein may also treat a viral and/or bacterial infection as a fungal or mycotic infection is being treated in a patient. In an embodiment, treatment of a patient using the compositions and methods encompassed herein may be deliberately used to treat a viral and/or bacterial infection in a patient, apart from treatment of a fungal or mycotic infection in a patient. By way of non-limiting examples, herpes simplex virus (HSV) and human papilloma virus (HPV) can be treated according to the methods and/or compositions disclosed herein. By way of another non-limiting example, an inguinal infection or condition can be treated according to the methods and/or compositions disclosed herein.

In an embodiment, the compositions and methods encompassed herein can be used to treat paronychia. Paronychia is an infection of the soft tissue surrounding the *unguis*, and may be associated with an ungual infection. Paronychia may involve infections of one or more of fungal, bacterial, and yeast origins. In an embodiment, compositions and/or methods encompassed herein are also useful for treating one or more of—but not limited to—verrucous warts, molluscum contagiosum, non-genital herpes simplex, scars, healing wounds, gram negative toe-web infection, psoriatic nail dystrophy, and tinea pedis. In an embodiment, such treatment encompasses treating the infection or infections present.

The compositions and methods are useful in treating one or any combination of at least two of the above diseases, conditions or pathogens.

Compositions

In an embodiment, a composition comprises at least one therapeutic agent and at least one solvent and/or penetrant. In an aspect, an iodophor is a therapeutic agent. In an embodiment, a composition comprises at least one antiseptic compound. In an aspect, an antiseptic compound is a therapeutic agent. In an embodiment, a composition comprises an iodophor antiseptic. "Iodophor", as used herein, refers to a substance comprising iodine and at least one additional agent (e.g., a solubilizing agent) that releases free iodine when in solution. Examples of iodophors include, but are not limited to, povidone iodine (PVP-I), iodine tincture, Lugol's solutions, and iodine salts (e.g., potassium iodide, sodium iodide).

In an embodiment, a composition comprises at least one iodophor. The compositions encompass any iodophor, as well as iodophors as yet to be developed or discovered. In an embodiment, the iodophor is PVP-I. In another embodiment, a composition comprises iodine. In an embodiment, a composition comprises iodine and at least one iodophor.

In an embodiment, PVP-I functions a therapeutic agent in a composition. In an aspect, a PVP-I therapeutic agent functions as an antiseptic. In another embodiment, PVP-I functions as a preservative in a composition. In an aspect, a PVP-I preservative functions as an antiseptic. In another aspect, a PVP-I preservative functions as a stabilizer. In an embodiment, PVP-I functions in at least once capacity in a composition. In another embodiment, PVP-I functions in at least two capacities in a composition.

In another embodiment, a composition further comprises at least one non-iodophor, non-iodine therapeutic agent. In an embodiment, the at least one non-iodophor, non-iodine therapeutic agent is an antiseptic. In another embodiment, the at least one non-iodophor, non-iodine therapeutic agent is not an antiseptic.

In an embodiment, the at least one non-iodophor, non-iodine therapeutic agent is an antifungal agent. Suitable antifungal agents include, for example, allylamines and azoles. In an embodiment, an antifungal agent includes, but is not limited to, tolnaftate, terbinafine, undecylenic acid, clioquinol, miconazole, miconazole nitrate, clorrinazole, tioconazole, nystatin, terconazoic, butoconazole nitrate, ciclopirox olamine, econazole nitrate, triacetin, flucytosine, haloprogin, and ketoconazole.

In an embodiment, a composition comprises one or more naturopathic substances. Naturopathic substances include, but are not limited to, *Punica Granatum* (Pomegranate) Extract, *Camellia Sinensis* Leaf (Green Tea) Extract, Ascorbic Acid (Vitamin-C), *Calendula Officinalis* Extract, *Glycrrhiza Glabra* (Licorice) Extract, Allantoin, and *Cucumis Sativus* (Cucumber) Fruit Extract. In an embodiment, a composition comprises DMSO, PVP-I, *Punica Granatum* (Pomegranate) Extract, *Camellia Sinensis* Leaf (Green Tea) Extract, Ascorbic Acid (Vitamin-C), *Calendula Officinalis* Extract, *Glycrrhiza Glabra* (Licorice) Extract, Allantoin, and *Cucumis Sativus* (Cucumber) Fruit Extract.

In an embodiment, a composition comprises at least one solvent and/or penetrant. In an embodiment, a single component may function as both a solvent and a penetrant in the composition. In an embodiment, a composition comprises DMSO. In an aspect, DMSO functions as a penetrant for the active component. In an aspect, DMSO functions as a solvent. In yet another aspect, DMSO functions as both a solvent and a penetrant. In an embodiment, DMSO is the sole penetrant in a composition. In an embodiment, DMSO is the sole solvent in a composition. In an embodiment, DMSO is the sole penetrant and solvent in a composition.

In an embodiment, a composition comprises PVP-I and DMSO. In another embodiment, a composition consists of PVP-I and DMSO. In yet another embodiment, a composition consists essentially of PVP-I and DMSO.

One of skill in the art will understand, based on the disclosure herein, how to identify a penetrant useful for the compositions and methods encompassed herein. In an embodiment, a penetrant is one which is useful for enabling the composition to penetrate the *unguis* or an affected area of the skin By way of a non-limiting example, methylsulfonylmethane may be used as a penetrant in a composition as encompassed herein.

In an embodiment, a composition comprises at least one co-solvent. In an embodiment, a composition comprises DMSO as a primary solvent, and further comprises at least one co-solvent. In an embodiment, water is a co-solvent. In an embodiment, a composition comprises DMSO as the primary solvent and water as a co-solvent. In an embodiment, a composition consists of DMSO as the primary solvent and water as the co-solvent. In another embodiment, a composition consists essentially of DMSO as the primary solvent and water as the co-solvent. In an embodiment, a composition comprises at least one co-solvent such as, but not limited to, water, or ethanol. In an embodiment, a co-solvent is one or more polar aprotic solvent. In an embodiment, a co-solvent is ethyl acetate. In an embodiment, a co-solvent is at least one of ethyl acetate, acetone, acetonitrile, tetrahydrofuran, methylene chloride, and dimethyl formamide. One of skill in the art will understand the advantages and limitations of the use of co-solvents, based on the properties and physical effects of such potential co-solvents, in view of the disclosure set forth herein. Other co-solvents are described in greater detail elsewhere herein.

In an embodiment, a composition comprises at least one excipient such as, but not limited to, sodium chloride, sodium dihydrogen phosphate monohydrate, disodium hydrogen phosphate anhydrous and water. The compositions encompassed herein will be understood to optionally include one or more other excipients as known to those skilled in the art. One of skill in the art will know how to identify such an excipient as useful in the present compositions and methods, for example, when such an excipient enhances the therapeutic effectiveness, stability, or potency of a composition or method. Other excipients are presented in greater detail elsewhere herein.

Dosages, Forms and Formulations

In an embodiment, a composition comprises a therapeutically effective amount of at least one therapeutic agent. The term "therapeutically effective amount" is used herein, unless otherwise indicated, to describe an amount of a compound which, in context, is used to produce or effect an intended therapeutic result. In an embodiment, the intended therapeutic result relates to the treatment of skin diseases complicated by microbial colonization and/or infection. In an embodiment, the intended therapeutic result relates to the treatment of onychomycosis. In an embodiment, a therapeutically effective amount is that amount which is sufficient to treat an ungual infection, and the treatment of the ungual infection includes at least one of preventing or slowing the progression of the infection, preventing the spread of the infection, eradicating at least some of the infection, and eradicating the entire infection. In an aspect, a therapeutically effective amount may be determined based on a single dosage or it may be determined based on multiple dosages of the composition. It will be understood that determination of the therapeutically effective amount may require trial and error, and may require adjustment of the dosage and or dosing regimen. Such therapeutic optimization and adjustment is encompassed by the methods encompassed herein.

The term "pharmaceutically acceptable", as used herein with respect to a compound or composition, refers to a form of the compound or composition that can increase or enhance the solubility or availability of the compound in a subject, in order to promote or enhance the bioavailability of the compound or composition. In an aspect, the disclosure herein also encompasses pharmaceutically acceptable, hydrates, solvates, stereoisomers, or amorphous solids of the compounds and compositions embodied herein.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 1990, incorporated herein by reference). Except insofar as any conventional carrier is incompatible with the active ingredient or method of use, its use in the pharmaceutical compositions is contemplated.

Percentages set forth herein are (w/w), with respect to the specified component in the overall composition, unless otherwise indicated. For example, a composition comprising 1% PVP-I and 99% DMSO has 1% PVP-I by weight, with respect to the total composition.

In an embodiment, a composition comprises an iodophor in the range of about 0.01% to about 15%. In another embodiment, a composition comprises an iodophor in the range between 0.05% and 12.5%. In another embodiment, a composition comprises an iodophor in the range between 0.05% and 10.0%. In another embodiment, a composition comprises an iodophor in the range between 0.1% and 10.0%. In another embodiment, a composition comprises an iodophor in the range between 0.1% and 5.0%. In another embodiment, a composition comprises an iodophor in the range between 0.25% and 9.0%. In another embodiment, a composition comprises an iodophor in the range between 0.2% and 2.5%. In another embodiment, a composition comprises an iodophor in the range between 0.5% and 7.5%. %. In another embodiment, a composition comprises an iodophor in the range between 0.5% and 1.0%. In another embodiment, a composition comprises an iodophor in the range between 0.75% and 5.0%, and in yet another embodiment, between 1.0% and 4.0%. In an embodiment, a composition comprises an iodophor in the range of about 0.1% to about 2.5%, about 0.2% to about 2.0%, about 0.3% to about 1.0%, and about 0.4% to about 0.75%.

In an embodiment, a composition comprises elemental iodine in the range of about 0.01% to about 15%. In another embodiment, a composition comprises elemental iodine in the range between 0.05% and 12.5%. In another embodiment, a composition comprises elemental iodine in the range between 0.05% and 10.0%. In another embodiment, a composition comprises elemental iodine in the range between 0.1% and 10.0%. In another embodiment, a composition comprises elemental iodine in the range between 0.1% and 5.0%. In another embodiment, a composition comprises elemental iodine in the range between 0.25% and 9.0%. In another embodiment, a composition comprises elemental iodine in the range between 0.2% and 2.5%. In another embodiment, a composition comprises elemental iodine in the range between 0.5% and 7.5%. %. In another embodiment, a composition comprises elemental iodine in the range between 0.5% and 1.0%. In another embodiment, a composition comprises elemental iodine in the range between 0.75% and 5.0%, and in yet another embodiment, between 1.0% and 4.0%. In an embodiment, a composition comprises elemental iodine in the range of about 0.1% to about 2.5%, about 0.2% to about 2.0%, about 0.3% to about 1.0%, and about 0.4% to about 0.75%.

In an embodiment, a composition comprises PVP-I in the range of about 0.01% to about 15%. In another embodiment, a composition comprises PVP-I in the range between 0.05% and 12.5%. In another embodiment, a composition comprises PVP-I in the range between 0.05% and 10.0%. In another embodiment, a composition comprises PVP-I in the range between 0.1% and 10.0%. In another embodiment, a composition comprises PVP-I in the range between 0.1% and 5.0%. In another embodiment, a composition comprises PVP-I in the range between 0.25% and 9.0%. In another embodiment, a composition comprises PVP-I in the range between 0.2% and 2.5%. In another embodiment, a composition comprises PVP-I in the range between 0.5% and 7.5%. %. In another embodiment, a composition comprises PVP-I in the range between 0.5% and 1.0%. In another embodiment, a composition comprises PVP-I in the range between 0.75% and 5.0%, and in yet another embodiment, between 1.0% and 4.0%. In an embodiment, a composition comprises PVP-I in the range of about 0.1% to about 2.5%, about 0.2% to about 2.0%, about 0.3% to about 1.0%, and about 0.4% to about 0.75%.

In an embodiment, a composition comprises PVP-I at about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1.0%, about 1.25%, about 1.50%, about 1.75%, about 2.0%, about 2.25%, about 2.5%, about 3.0%, about 3.5%, about 4%, about 4.5%, about 5%, about 7.5%, about 10%, about 12.5, or about 15.0%. In an embodiment, a composition comprises PVP-I at 0.001%, 0.005%, 0.01%, 0.05%, 0.1%, 0.2%, 0.3%, 0.4%, 0.5%, 0.6%, 0.7%, 0.8%, 0.9%, 1.0%, 1.25%, 1.5%, 1.75%, 2.0%, 2.25%, 2.5%, 3.0%, 3.5%, 4.0%, 4.5%, 5%, 7.5%, 10.0%, 12.5%, or 15%. In another embodiment, a composition comprises PVP-I at about 1%, about 2%, about 3%, about 4%, about 5%, about 6%, about 7%, about 8%, about 9%, about 10%. In another embodiment, a composition comprises PVP-I at about 0.1% or less, about 0.5% or less, about 1% or less, about 2% or less, about 3% or less, about 4% or less, about 5% or less, about 6% or less, about 7% or less, about 8% or less, about 9% or less or about 10% or less. In another embodiment, a composition comprises PVP-I at about 0.01% or more, about 0.05% or more, about 0.075% or more, about 0.1% or more, about 0.2% or more, about 0.3% or more, about 0.4% or more, about 0.5% or more, about 0.6% or more, about 0.7% or more, about 0.8% or more, about 0.9% or more, about 1% or more, about 2% or more, about 3% or more, about 4% or more, about 5% or more, about 6% or more, about 7% or more, about 8% or more, about 9% or more or about 10% or more. In another embodiment, a composition comprises PVP-I at 0.001%, 0.005%, 0.01%, 0.05%, 0.1%, 0.2%, 0.3%, 0.4%, 0.5%, 0.6%, 0.7%, 0.8%, 0.9%, 1.0%, 1.25%, 1.5%, 1.75%, 2.0%, 2.25%, 2.5%, 2.75%, 3.0%, 3.5%, 4.0%, 4.5%, 5.0%, 6.0%, 7.0%, 8.0%, 9.0% or 10.0%.

In an embodiment, a composition comprises DMSO and PVP-I. In an embodiment, a composition consists essentially of DMSO and PVP-I. In an embodiment, a composition consists of DMSO and PVP-I. In an embodiment, a composition is anhydrous. In an embodiment, a composition is substantially anhydrous. In an embodiment, a composition comprises a measurable amount of water. In an embodiment, a composition comprises no measurable amount of water.

In an embodiment, anhydrous DMSO is used in a composition. In an embodiment, substantially anhydrous DMSO is used in a composition. It will be understood by one of skill in the art that DMSO can be produced and/or obtained in differing grades, and that one of the variables among DMSO preparations of different grades is the water content. By way of example, DMSO may be completely anhydrous (also referred to herein simply as "anhydrous"), substantially anhydrous, or may contain water to a measurable degree. It will be understood that the amount of measurable water in a DMSO preparation may vary based on limitations of the instrumentation and techniques used to make such measurements. In an embodiment, DMSO that is not completely anhydrous may be substantially anhydrous and contain water at a level below levels of detectability. In an embodiment, DMSO that is not completely anhydrous may contain water, wherein the water content is about at least 0.01%, about at least 0.02%, about at least 0.03%, about at least 0.04%, about at least 0.05%, about at least 0.06%, about at least 0.07%, about at least 0.08%, about at least 0.09%, about at least 0.1%, about at least 0.2%, about at least 0.3%, about at least 0.4%, about at least 0.5%, about at least 0.6%, about at least 0.7%, about at least 0.8%, about at least 0.9%, about at least 1.0%, about at least 1.5%, about at least 2.0%, about at least 2.5%, about at least 5%, about at least 7.5%, about at least 10%, about at least 12.5%, or greater. In an embodiment, DMSO that is not completely anhydrous may contain water, wherein the water content is about less than 0.01%, about less than 0.02%, about less than 0.03%, about less than 0.04%, about less than 0.05%, about less than 0.06%, about less than 0.07%, about less than 0.08%, about less than 0.09%, about less than 0.1%, about less than 0.2%, about less than 0.3%, about less than 0.4%, about less than 0.5%, about less than 0.6%, about less than 0.7%, about less than 0.8%, about less than 0.9%, about less than 1.0%, about less than 1.5%, about less than 2.0%, about less than 2.5%, about less than 5%, about less than 7.5%, about less than 10%, about less than 12.5%, or greater. It will be understood that DMSO may contain one or more other impurities in addition to water.

In an embodiment, a composition comprises an iodophor, a penetrant, and further comprises water. In an embodiment, a composition comprises an anyhydrous iodophor and/or an anyhydrous penetrant, and further comprises water. In an embodiment, a composition comprises PVP-I, DMSO, and further comprises water. In an embodiment, a composition comprises an iodophor and a penetrant, and further comprises water, wherein the water content is about at least 0.01%, about at least 0.02%, about at least 0.03%, about at least 0.04%, about at least 0.05%, about at least 0.06%, about at least 0.07%, about at least 0.08%, about at least 0.09%, about at least 0.1%, about at least 0.2%, about at least 0.3%, about at least 0.4%, about at least 0.5%, about at least 0.6%, about at least 0.7%, about at least 0.8%, about at least 0.9%, about at least 1.0%, about at least 1.5%, about at least 2.0%, about at least 2.5%, about at least 5%, about at least 7.5%, about at least 10%, about at least 12.5%, or greater. In an embodiment, a composition comprises an iodophor and a penetrant, and further comprises water, wherein the water content is about less than 0.01%, about less than 0.02%, about less than 0.03%, about less than 0.04%, about less than 0.05%, about less than 0.06%, about less than 0.07%, about less than 0.08%, about less than 0.09%, about less than 0.1%, about less than 0.2%, about less than 0.3%, about less than 0.4%, about less than 0.5%, about less than 0.6%, about less than 0.7%, about less than 0.8%, about less than 0.9%, about less than 1.0%, about less than 1.5%, about less than 2.0%, about less than 2.5%, about less than 5%, about less than 7.5%, about less than 10%, about less than 12.5%, or greater. In an embodiment, a composition comprises an iodophor and a penetrant, and further comprises water, wherein the water content is about 0.01% to about 12.5%, about 0.02% to about 10.0%, about 0.03% to about 7.5%, about 0.04% to about 5%, about 0.05% to about 2.5%, about 0.06% to about 2%, about 0.07% to about 1.5%, about 0.08% to about 1%, about 0.09% to about 0.9%, about 0.1% to about 0.8%, or about 0.2% to about 0.7%. In an aspect, the water may be derived from a component of the composition. In another aspect, the water may be specifically added to the composition.

In an embodiment, a composition comprises at least one of United States Pharmacopeial Convention (USP) grade DMSO, Active Pharmaceutical Ingredient (API) grade DMSO, analytical grade DMSO, and American Chemical Society (ACS) Spectrophotometric grade DMSO. In an embodiment, a composition comprises DMSO having <0.1% water by KF titration and >99.9% determined on an anyhdrous basis.

As set forth above, the percent amount of DMSO in a composition is described in a weight-to-weight (w/w) ratio with respect to one or more other components of the composition, unless otherwise indicated. In an embodiment, the weight percent DMSO is the balance of the weight percent after addition of PVP-I. By way of a non-limiting example, a composition may comprise 1 weight percent (1%) PVP-I and 99 weight percent (99%) DMSO. It will be understood that in the foregoing example, the DMSO component of the composition may be completely anhydrous, substantially anhydrous, or may contain water to a measurable degree. In an embodiment, the weight percent DMSO is the balance of the weight percent after addition of PVP-I and any other components (e.g., co-solvent, water, additional active ingredient, etc. . . . ). In an embodiment, the weight percent DMSO is the balance of the weight percent after addition of iodophor and other components, if any. In an embodiment, the weight percent penetrant in a composition is the balance of the weight percent after addition of iodophor and other components, if any.

In an embodiment, a composition comprises DMSO in the range of 50% to 99.99%. In an embodiment, a composition comprises DMSO in the range of 1% to 99.99%. In another embodiment, a composition comprises DMSO in the range of 5% and 99.9%. In another embodiment, a composition comprises DMSO in the range of 10% and 99.9%. In another embodiment, a composition comprises DMSO in the range of 20% and 99.9%. In another embodiment, a composition comprises DMSO in the range of 30% and 99.9%. In another embodiment, a composition comprises DMSO in the range of 40% and 99.9%. In another embodiment, a composition comprises DMSO in the range of 50% and 99.9%. In another embodiment, a composition comprises DMSO in the range of 60% and 99.9%. In another embodiment, a composition comprises DMSO in the range of 70% and 99.9%. In another embodiment, a composition comprises DMSO in the range of 80% and 99.9%, and in yet another embodiment, between 90% and 99.9%.

In an embodiment, a composition comprises DMSO in weight percent of about at least 50%, about at least 55%, about at least 60%, about at least 65%, about at least 70%, about at least 75%, about at least 80%, about at least 85%, about at least 87.5%, about at least 90%, about at least 91%, about at least 92%, about at least 93%, about at least 94%, about at least 95%, about at least 96%, about at least 97%, about at least 98%, about at least 99%, or about at least 99.9%. In an embodiment, a composition comprises DMSO at about 1%. In other embodiments, a composition comprises DMSO at about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.5%, or about 99.9%.

In an embodiment, a composition comprises DMSO but does not comprise any additional solvent (e.g., co-solvent) or penetrant. In another embodiment, a composition comprises DMSO in the range of about 0.01% to 99.99% and further comprises at least one co-solvent in the range of 0.01% to about 99.99%. In an embodiment, a composition comprises DMSO and further comprises at least one co-solvent in the range of about 0.1% to about 50%. In another embodiment, a composition comprises DMSO and further comprises at least one co-solvent in the range between about 5% and about 50%. In another embodiment, a composition comprises DMSO and further comprises at least one co-solvent in the range between about 10% and about 99%. In another embodiment, a composition comprises DMSO and further comprises at least one co-solvent in the range between about 20% and about 95%. In an embodiment, a composition comprises DMSO and further comprises at least one co-solvent in the range of about 50% to about 60%, about 60% to about 80%, about 70% to about 90%, and about 80% to about 95%. In an aspect, water is a co-solvent. In an embodiment, a composition comprises DMSO, water, and at least one additional co-solvent. In an embodiment, a composition comprises DMSO, water, and at least two additional co-solvents. In an embodiment, a composition is substantially anhydrous and comprises DMSO and at least one additional co-solvent.

In an embodiment, a composition comprises a co-solvent in the range of 1% to 99.99%. In another embodiment, a composition comprises a co-solvent in the range of 5% and 99.9%. In another embodiment, a composition comprises a co-solvent in the range of 10% and 99.9%. In another embodiment, a composition comprises a co-solvent in the range of 20% and 99.9%. In another embodiment, a composition comprises a co-solvent in the range of 30% and 99.9%. In another embodiment, a composition comprises a co-solvent in the range of 40% and 99.9%. In another embodiment, a composition comprises a co-solvent in the range of 50% and 99.9%. In another embodiment, a composition comprises a co-solvent in the range of 60% and 99.9%. In another embodiment, a composition comprises a co-solvent in the range of 70% and 99.9%. In another embodiment, a composition comprises a co-solvent in the range of 80% and 99.9%, and in yet another embodiment, between 90% and 99.9%.

In an embodiment, a composition comprises a co-solvent at about 1%. In other embodiments, a composition comprises a co-solvent at about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%.

Examples of co-solvents include, but are not limited to, alcohols, silicones, polyglycols, glycols, and combinations thereof. In an embodiment, a co-solvent is diethyleneglycol monoethyl ether (DGMEE). In an embodiment, a co-solvent is propylene glycol.

In an embodiment, a composition comprises DMSO in the range of about 0.01% to 99.99% and further comprises at least one penetrant in the range of 0.01% to about 99.99%. In an embodiment, a composition comprises DMSO and further comprises at least one penetrant in the range of about 0.1% to about 50%. In another embodiment, a composition comprises DMSO and further comprises at least one penetrant in the range between about 5% and about 50%. In another embodiment, a composition comprises DMSO and further comprises at least one penetrant in the range between about 10% and about 99%. In an embodiment, a composition comprises DMSO, at least one co-solvent, and at least one penetrant. In an embodiment, a co-solvent is also a penetrant.

In an embodiment, a composition includes at least one antifungal agent selected from the group consisting of tolnaftate, terbinafine, undecylenic acid, clioquinol, miconazole, miconazole nitrate, clorrinazole, tioconazole, nystatin, terconazoic, butoconazole nitrate, ciclopirox olamine, econazole nitrate, triacetin, flucytosine, haloprogin, and ketoconazole. In an embodiment, the at least one antifungal agent is present of about 0.01%, about 0.05%, about 0.1%, about 0.2%, about 0.3%, about 0.4%, about 0.5%, about 0.6%, about 0.7%, about 0.8%, about 0.9%, about 1.0%, about 1.25%, about 1.50%, about 1.75%, about 2.0%, about 2.5%, about 5%, about 7.5%, about 10%, about 12.5, about 15.0%, about 20%, about 25%, about 30%, about 40%, or about 50%. In an embodiment, a composition comprises the at least one antifungal agent of 0.01%, 0.05%, 0.1%, 0.2%, 0.3%, 0.4%, 0.5%, 0.6%, 0.7%, 0.8%, 0.9%, 1.0%, 1.25%, 1.5%, 1.75%, 2.0%, 2.25%, 2.5%, 5%, 7.5%, 10.0%, 12.5%, 15%, 20%, 25%, 30%, 40%, or 50%. In another embodiment, a composition comprises the at least one antifungal agent of about 0.1% or less, about 0.5% or less, about 1% or less, about 2% or less, about 3% or less, about 4% or less, about 5% or less, about 6% or less, about 7% or less, about 8% or less, about 9% or less, about 10% or less, about 20% or less, about 25% or less, about 30% or less, about 40% or less, or about 50% or less. In another embodiment, a composition comprises the at least one antifungal agent of about 0.1% or more, about 0.5% or more, about 1% or more, about 2% or more, about 3% or more, about 4% or more, about 5% or more, about 6% or more, about 7% or more, about 8% or more, about 9% or more, about 10% or more, about 20% or more, about 25% or more, about 30% or more, about 40% or more, or about 50% or more. In another embodiment, a composition comprises the at least one antifungal agent of 0.01%, 0.05%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 20%, 25%, 30%, 40%, or 50%.

In an embodiment, stable preparations of at least one topical anti-fungal ingredient known in the art including, by way of non-limiting example, 1% tolnaftate, 10-25% undecylenic acid, clioquinol 3% and/or miconazole nitrate 2%, can be prepared in DMSO solvent systems where PVP-I is also incorporated as a long-term preservative. These solutions demonstrate remarkable long-term stability where both the PVP-I component and the anti-fungal component are able to be maintained at or above 90% of the initial concentrations. It is surprisingly found that no appreciable reaction occurs between the antifungal agent and the PVP-I. These formulations also demonstrate remarkable in vitro and in vivo efficacy as antifungal agents.

In an embodiment, where possible, compositions may include pharmaceutically acceptable salts of compounds in the composition. In an embodiment, compositions comprise acid addition salts of the present compounds. In an embodiment, compositions comprise base addition salts of the present compounds. As used herein, the term pharmaceutically acceptable salts or complexes refers to salts or complexes (e.g., solvates, polymorphs) that retain the desired biological activity of the parent compound and exhibit minimal, if any, undesired toxicological effects.

In various embodiments, the compositions encompassed herein comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Demulcents include, but are not limited to, benzoin, hydroxypropyl cellulose, hydroxypropyl methylcellulose, and polyvinyl alcohol.

Emollients include, but are not limited to, animal and vegetable fats and oils, myristyl alcohol, alum, and aluminum acetate.

Preservatives include, but are not limited to, chlorine dioxide, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

In an embodiment, a composition comprises PVP-I, DMSO, diethylene glycol monoethyl ether, and propylene glycol. In an embodiment, a composition comprises 2% PVP-I, 65% DMSO, 23% diethylene glycol monoethyl ether, and 10% propylene glycol. In an embodiment, the composition is substantially anhydrous. In an embodiment, the composition is anhydrous.

In an embodiment, a composition comprises PVP-I, DMSO, and diethylene glycol monoethyl ether. In an embodiment, a composition comprises 2% PVP-I, 65% DMSO, and 33% diethylene glycol monoethyl ether. In an embodiment, the composition is substantially anhydrous. In an embodiment, the composition is anhydrous.

Methods of Preparation and Use

It is known to one of skill in the art that PVP-I aqueous solutions are difficult to stabilize at low PVP-I concentrations over a long period of time. By way of a non-limiting example, at concentrations of PVP-I less than about 0.7% (w/w, aqueous), PVP-I aqueous solutions rapidly decay to yield complex mixtures of iodinated and iodine-free constituents. As described herein, it was surprisingly found that in the aprotic DMSO solvent system encompassed by the disclosure set forth herein, PVP-I solutions as low as 0.1% can be easily prepared and maintained as stable compositions for long periods of time. Also as described herein, hydrated DMSO solutions prepared from aqueous PVP-I demonstrate increased stability is noted for the PVP-I component.

In an embodiment, a composition comprises dry, solid or powdered PVP-I dissolved or suspended in a composition comprising or consisting of DMSO. In another embodiment, DMSO is added to an aqueous preparation comprising or consisting of PVP-I. Based on the disclosure herein, one of skill in the art will understand how to prepare a composition to arrive at the desired amounts of iodine, iodophor, and DMSO, among other possible components of the compositions encompassed herein.

By way of a non-limiting example, a therapeutically-effective pharmaceutical composition is prepared using solid PVP-I, which is dissolved or suspended in DMSO. In an aspect, the composition is anhydrous. In an aspect, the composition is substantially anhydrous. In another embodiment, DMSO can be added to aqueous solutions of PVP-I to prepare a therapeutically-effective pharmaceutical composition. In an embodiment, DMSO is used in the range of 50%-99% as a co-solvent with water. In an embodiment, a formulation includes one or more excipients. By way of a non-limiting example, excipients include, but are not limited to, sodium chloride, sodium dihydrogen phosphate monohydrate, disodium hydrogen phosphate anhydrous and water, as well as others known to those skilled in the art.

In an embodiment, a composition is prepared by adding 10% PVP-I (w/v, aqueous) to pure DMSO q.s. to yield a resulting solution of 1% PVP-I (w/w) with DMSO. In another embodiment, compositions are prepared by dissolving solid PVP-I in pure DMSO q.s to obtain any of 0.1%, 0.2%, 0.3%, 0.4%, 0.5%, 1.0%, 1.25%, 1.5%, 2.0%, or 2.5% PVP-I (w/w), as well as about 0.1%, about 0.2%, about 0.3%, about 0.4%, about 0.5%, about 1.0%, about 1.25%, about 1.5%, about 2.0%, or about 2.5% PVP-I (w/w) compositions, with DMSO as the solvent. In yet another embodiment, compositions are prepared by dissolving solid PVP-I in pure DMSO q.s to obtain any composition set forth, described, and/or encompassed herein. Similar compositions comprising aqueous PVP-I (with and without excipients commonly used and/or known in the art) and DMSO can be prepared from a stock 10% PVP-I aqueous solution and pure DMSO. It will be understood by the skilled artisan, however, that any starting composition of PVP-I, solid or liquid, may be used when the appropriate dilutions and adjustments are made to result in the desired final PVP-I concentration. Similarly, any starting composition of iodophor or elemental iodine may be used when the appropriate dilutions and adjustments are made to result in the desired final iodophor or elemental iodine concentration, respectively.

In an embodiment, it is particularly useful for the case of ungual infections that stable, anhydrous compositions that contain between 0.01%-10% PVP-I can be prepared in pure USP grade DMSO solvents.

It will be understood, based on the disclosure set forth herein, in view of the skill in the art, that specific dosage for compounds and compositions encompassed herein may be determined empirically through clinical and/or pharmacokinetic experimentation, and that such dosages may be adjusted according to prespecified effectiveness and/or toxicity criteria. It will also be understood that a specific dosage and treatment regimen for any particular patient will depend upon a variety of factors, including the activity of the specific compounds employed, the characteristics of the patient, drug combination, the judgment of the treating physician and the nature and severity of the particular disease or condition being treated.

In an embodiment, a composition set forth, described, and/or encompassed herein is useful for treating one or more of—but not limited to—onychomycosis, paronychia, verrucous warts, molluscum contagiosum, non-genital herpes simplex, scars, healing wounds, gram negative toe-web infection, psoriatic nail dystrophy, tinea pedis, molluscum contagiousum, seborrheic dermatitis, hand dermatitis, atopic dermatitis, acne, rosacea, and verruca vulgaris. In an embodiment, the composition comprises PVP-I and DMSO. In an embodiment, the composition consists essentially of PVP-I and DMSO. In an embodiment, the composition consists of PVP-I and DMSO.

In an embodiment, a therapeutic composition is prepared by optimizing one or more compounds for use in a dosage form different than that which is typically used for the compound. In an embodiment, a compound that is not typically administered in a topical dosage form is developed for use in a topical dosage form. The chemical and biological assays required for such development are known to one of skill in the art. The disclosure herein provides the skilled artisan with the guidance as to how to prepare such compounds and compositions comprising such compounds.

In an embodiment, a method of treating a subject having an ungual infection includes administration of a composition set forth, described, and/or encompassed herein to treat the ungual infection, and the treatment of the ungual infection includes at least one of preventing or slowing the progression of the infection, preventing the spread of the infection, eradicating at least some of the infection, and eradicating the entire infection.

In an embodiment, a method of treating a subject having a skin disease complicated by microbial colonization and/or infection includes administration of a composition set forth, described, and/or encompassed herein to treat the skin disease, and the treatment of the skin disease includes at least one of preventing or slowing the progression of the infection, preventing the spread of the infection, eradicating at least some of the infection, and eradicating the entire infection.

In an embodiment, a therapeutic composition is administered on a schedule once a day. In an embodiment, a therapeutic composition is administered twice a day. In an embodiment, a therapeutic composition is administered three times a day, four times a day, five times a day, or more. In an embodiment, a therapeutic composition is administered less frequently than once a day. In an embodiment, a therapeutic composition is administered once every two days, once every three days, once every four days, once every five days, once every six days, or once every seven days. In an embodiment, a therapeutic composition is administered less frequently than once a week. In an embodiment, a therapeutic composition is administered once a month. In an embodiment, a therapeutic composition is administered twice a month.

In an embodiment, a therapeutic dosing regimen is continued for at least one day, at least two days, at least three days, at least four days, at least five days, at least six days, or at least seven days. In an embodiment, a therapeutic dosing regimen is continued for at least one week, at least two weeks, at least three weeks, at least four weeks, at least six weeks, at least eight weeks, at least ten weeks, at least twelve weeks, at least fourteen weeks, or at least sixteen weeks. In an embodiment, a therapeutic dosing regimen is continued for at least one month, at least two months, at least three months, at least four months, at least five months, at least six months, at least nine months, or at least twelve months.

The invention is further described by the following examples. In an aspect, the following examples demonstrate effective and/or successful treatment of the identified conditions using compositions and methods encompassed by the present disclosure. It should be recognized that variations based on the inventive features are within the skill of the ordinary artisan, and that the scope of the invention should not be limited by the examples. To properly determine the scope of the invention, an interested party should consider the claims herein, and any equivalent thereof. In addition, all citations herein are incorporated by reference, and unless otherwise expressly stated, all percentages are by weight.

Example 1: Distal Subungual Onychomycosis; Treated with 1% PVP-I in 99% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 25 years. The patient had tried numerous prescription and OTC remedies. Pre-treatment cultures were positive for *Tryco-*

*phyton mentagrophytes.* Prepared was a composition as disclosed herein using 1% PVP-I in 99% USP Grade DMSO with no additional water or alcohols. The patient was treated by applying the solution topically twice each day to the nail itself and the surrounding skin with a nailbrush. Within one week improvement was noted in the surrounding skin infection. After 2 weeks of treatment the cultures were repeated and were found to be negative. The affected nail plate began to separate from the underlying nail bed and was removed with scissors. The underlying nail bed appeared to be normal and free of infection. The new nail began to grow in free of infection in above the uninfected nail bed. After 20 weeks of treatment at least 5 mm of clear nail could be seen growing free of infection.

Example 2: Distal Subungual Onychomycosis; Treated with 0.5% PVP-I in 99.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 25 years. The patient had tried numerous prescription and OTC remedies. Pre-treatment cultures were positive for *Trycophyton mentagrophytes.* Prepared was a composition as disclosed herein using 1% PVP-I in 99.5% USP Grade DMSO with no additional water or alcohols. The patient was treated by applying the solution topically twice each day to the nail itself and the surrounding skin with a nailbrush. Within one week improvement was noted in the surrounding skin infection. After 2 weeks of treatment the cultures were repeated and were found to be negative. The affected nail plate began to separate from the underlying nail bed and was removed with scissors. The underlying nail bed appeared to be normal and free of infection. The new nail began to grow in free of infection in above the uninfected nail bed. After 20 weeks of treatment at least 5 mm of clear nail could be seen growing free of infection.

Example 3: Distal Subungual Onychomycosis; Treated with 1.5% PVP-I in 98.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 5 years. The patient had tried numerous prescription and OTC remedies. Pre-treatment cultures were positive for *Trycophyton mentagrophytes.* Prepared was a composition as disclosed herein using 1.5% PVP-I in 98.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 4: Distal Subungual Onychomycosis; Treated with 2.0% PVP-I in 98% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 3 years. The patient had tried numerous prescription and OTC remedies. Pre-treatment cultures were positive for *Trycophyton mentagrophytes.* Prepared was a composition as disclosed herein using 2.0% PVP-I in 98% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 5: Distal Subungual Onychomycosis; Treated with 2.5% PVP-I in 97.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 4 years. The patient had tried numerous prescription and OTC remedies. Pre-treatment cultures were positive for *Trycophyton rubrum.* Prepared was a composition as disclosed herein using 2.5% PVP-I in 97.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 6: Distal Subungual Onychomycosis; Treated with 3.0% PVP-I in 97% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 10 years. The patient had tried numerous prescription and OTC remedies. Pre-treatment cultures were positive for *Trycophyton rubrum*. Prepared was a composition as disclosed herein using 3.0% PVP-I in 97% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 7: Distal Subungual Onychomycosis; Treated with 3.5% PVP-I in 96.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 2 years. The patient had tried numerous prescription and OTC remedies. Pre-treatment cultures were positive for *Trycophyton mentagrophytes*. Prepared was a composition as disclosed herein using 3.5% PVP-I in 96.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 8: Distal Subungual Onychomycosis; Treated with 4.0% PVP-I in 96% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 2 years. The patient had tried numerous prescription and OTC remedies. Pre-treatment cultures were positive for *Trycophyton rubrum*. Prepared was a composition as disclosed herein using 4.0% PVP-I in 96% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 9: Distal Subungual Onychomycosis; Treated with 4.5% PVP-I in 95.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 7 years. The patient had tried numerous prescription and OTC remedies. Pre-treatment cultures were positive for *Trycophyton mentagrophytes*. Prepared was a composition as disclosed herein using 4.5% PVP-I in 95.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 10: Distal Subungual Onychomycosis; Treated with 5.0% PVP-I in 95% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 5 years. The patient had tried numerous prescription and OTC remedies. Pre-treatment cultures were positive for *Trycophyton metagrophytes*. Prepared was a composition as disclosed herein using 5.0% PVP-I in 95% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 11: Distal Subungual Onychomycosis; Treated with 5.5% PVP-I in 94.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 4 years. The patient had tried numerous prescription and OTC remedies. Pre-treatment cultures were positive for *Trycophyton metagrophytes*. Prepared was a composition as disclosed herein using 5.5% PVP-I in 94.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 12: Distal Subungual Onychomycosis; Treated with 6.0% PVP-I in 94% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 5 years. The patient had tried numerous prescription and OTC remedies. Pre-treatment cultures were positive for *Trycophyton mentagrophytes*. Prepared was a composition as disclosed herein using 6.0% PVP-I in 94% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 13: Distal Subungual Onychomycosis; Treated with 6.5% PVP-I in 93.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 10 years. The patient had tried numerous prescription and OTC remedies. Pre-treatment cultures were positive for *Trycophyton rubrum*. Prepared was a composition as disclosed herein using 6.5% PVP-I in 93.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 14: Distal Subungual Onychomycosis; Treated with 7.0% PVP-I in 93% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 3 years. The patient had tried numerous prescription and OTC remedies. Pre-treatment cultures were positive for *Trycophyton metagrophytes*. Prepared was a composition as disclosed herein using 7.0% PVP-I in 93% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 15: Distal Subungual Onychomycosis; Treated with 7.5% PVP-I in 92.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 13 years. The patient had tried numerous prescription and OTC remedies. Pre-treatment cultures were positive for *Trycophyton metagrophytes*. Prepared was a composition as disclosed herein using 7.5% PVP-I in 92.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 16: Distal Subungual Onychomycosis; Treated with 8.0% PVP-I in 92% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 6 years. The patient had tried numerous prescription and OTC remedies. Pre-treatment cultures were positive for *Trycophyton metagrophytes*. Prepared was a composition as disclosed herein using 8.0% PVP-I in 92% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 17: Distal Subungual Onychomycosis; Treated with 8.5% PVP-I in 91.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 6 years. The patient had tried numerous prescription and OTC remedies. Pre-treatment cultures were positive for *Trycophyton metagrophytes*. Prepared was a composition as disclosed herein using 8.5% PVP-I in 91.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 18: Distal Subungual Onychomycosis; Treated with 9.0% PVP-I in 91% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 18 years. The patient had tried numerous prescription and OTC remedies. Pre-treatment cultures were positive for *Trycophyton metagrophytes*. Prepared was a composition as disclosed herein using 9.0% PVP-I in 91% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 19: Distal Subungual Onychomycosis; Treated with 9.5% PVP-I in 90.5% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 1 year. The patient had tried numerous prescription and OTC remedies. Pre-treatment cultures were positive for *Trycophyton metagrophytes*. Prepared was a composition as disclosed herein using 9.5% PVP-I in 90.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 20: Distal Subungual Onychomycosis; Treated with 10.0% PVP-I in 90% USP Grade DMSO with No Additional Water or Alcohol or Co-Solvents This patient was suffering from distal subungual onychomycosis. In this most common type of onychomycosis, the end of the nail plate becomes discolored, thickened and often malodorous. Often the periungual skin is affected. In this patient, the condition had been persistent for over 3 years. The patient had tried numerous prescription and OTC remedies. Pre-treatment cultures were positive for *Trycophyton metagrophytes*. Prepared was a composition as disclosed herein using 10.0% PVP-I in 90% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 21: White Superficial Onychomycosis; Treated with 0.5% PVP-I in 99.5% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 2 years. The patient had tried numerous prescription and OTC remedies. Pre-treatment cultures were positive for *Trycophyton rubrum*. Prepared was a composition as disclosed herein using 0.5% PVP-I in 99.5% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 22: White Superficial Onychomycosis; Treated with 1.0% PVP-I in 99% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 4 years. The patient had tried numerous prescription and OTC remedies. Pre-treatment cultures were positive for *Trycophyton rubrum*. Prepared was a composition as disclosed herein using 1.0% PVP-I in 99% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 23: White Superficial Onychomycosis; Treated with 1.5% PVP-I in 98.5% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 3 years. The patient had tried numerous prescription and OTC remedies. Pre-treatment cultures were positive for *Trycophyton mentagrophytes*. Prepared was a composition as disclosed herein using 1.5% PVP-I in 98.5% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 24: White Superficial Onychomycosis; Treated with 2.0% PVP-I in 98% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 3 years. The patient had tried numerous prescription and OTC remedies. Pre-treatment cultures were positive for *Trycophyton rubrum*. Prepared was a composition as disclosed herein using 2.0% PVP-I in 98% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 25: White Superficial Onychomycosis; Treated with 2.5% PVP-I in 97.5% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 2 years. The patient had tried numerous prescription and OTC remedies. Pre-treatment cultures were positive for *Trycophyton mentagrophytes*. Prepared was a composition as disclosed herein using 2.5% PVP-I in 97.5% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 26: White Superficial Onychomycosis; Treated with 3.0% PVP-I in 97% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 1 year. The patient had tried numerous prescription and OTC remedies. Pre-treatment cultures were positive for *Trycophyton rubrum*. Prepared was a composition as disclosed herein using 3.0% PVP-I in 97% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 27: White Superficial Onychomycosis; Treated with 10% PVP-I in 90% USP Grade DMSO with No Additional Water or Alcohol or Co-Solvents This patient was suffering from white superficial onychomycosis. This is a less common subtype of onychomycosis in which the fungus only invades the most superficial portion of the nail plate and does not invade the nail bed or underlying surface of the nail. The dorsal portion of the nail plate appears chalky white. The surrounding skin is not typically affected. In this patient, the condition had been present for over 2 years. The patient had tried numerous prescription and OTC remedies. Pre-treatment cultures were positive for *Trycophyton rubrum*. Prepared was a composition as disclosed herein using 10% PVP-I in 90% USP Grade DMSO with no additional water or alcohols. The patient was treated by applying the solution topically twice each day to the nail itself and the surrounding skin with a nailbrush. After 12 weeks of treatment the cultures were repeated and were found to be negative. The affected nail plate changed from chalky white to a normal appearing nail as it grew out from the matrix. The underlying nail bed appeared to be normal and free of infection. The new nail began to grow in free of infection in above the uninfected nail bed. After 20 weeks of treatment at least 5 mm of clear nail could be seen growing free of infection.

Example 28: Total Dystrophic Onychomycosis; Treated with 0.5% PVP-I in 99.5% USP Grade DMSO with No Additional Water or Alcohol or Co-Solvents This patient was suffering from total dystrophic onychomycosis. In this most recalcitrant subtype of onychomycosis, the entire nail plate becomes dystrophic. It demonstrates a severely thickened, discolored, often malodorous infection. Nail matrix involvement and dermatophytomas are frequently present. Commonly the periungual and interdigital skin are affected. In this patient, the condition had been persistent for over 18 years. The patient had tried numerous prescription and OTC remedies. Pre-treatment cultures were positive for *Trichophyton metagrophytes*. Prepared was a composition as disclosed herein using 0.5% PVP-I in 99.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 29: Total Dystrophic Onychomycosis; Treated with 1.0% PVP-I in 99% USP Grade DMSO with No Additional Water or Alcohol or Co-Solvents This patient was suffering from total dystrophic onychomycosis. In this most recalcitrant subtype of onychomycosis, the entire nail plate becomes dystrophic. It demonstrates a severely thickened, discolored, often malodorous infection. Nail matrix involvement and dermatophytomas are frequently present. Commonly the periungual and interdigital skin are affected. In this patient, the condition had been persistent for over 8 years. The patient had tried numerous prescription and OTC remedies. Pre-treatment cultures were positive for *Trichophyton metagrophytes*. Prepared was a composition as disclosed herein using 1.0% PVP-I in 99% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 30: Total Dystrophic Onychomycosis; Treated with 1.5% PVP-I in 98.5% USP Grade DMSO with No Additional Water or Alcohol or Co-Solvents This patient was suffering from total dystrophic onychomycosis. In this most recalcitrant subtype of onychomycosis, the entire nail plate becomes dystrophic. It demonstrates a severely thickened, discolored, often malodorous infection. Nail matrix involvement and dermatophytomas are frequently present. Commonly the periungual and interdigital skin are affected. In this patient, the condition had been persistent for over 3 years. The patient had tried numerous prescription and OTC remedies. Pre-treatment cultures were positive for *Trichophyton metagrophytes*. Prepared was a composition as disclosed herein using 1.5% PVP-I in 98.5% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 31: Total Dystrophic Onychomycosis; Treated with 2.0% PVP-I in 98% USP Grade DMSO with No Additional Water or Alcohol or Co-Solvents This patient was suffering from total dystrophic onychomycosis. In this most recalcitrant subtype of onychomycosis, the entire nail plate becomes dystrophic. It demonstrates a severely thickened, discolored, often malodorous infection. Nail matrix involvement and dermatophytomas are frequently present. Commonly the periungual and interdigital skin are affected. In this patient, the condition had been persistent for over 4 years. The patient had tried numerous prescription and OTC remedies. Pre-treatment cultures were positive for *Trichophyton rubrum*. Prepared was a composition as disclosed herein using 2.0% PVP-I in 98% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 32: Total Dystrophic Onychomycosis; Treated with 2.5% PVP-I in 97.5% USP Grade DMSO with No Additional Water or Alcohol or Co-Solvents This patient was suffering from total dystrophic onychomycosis. In this most recalcitrant subtype of onychomycosis, the entire nail plate becomes dystrophic. It demonstrates a severely thickened, discolored, often malodorous infection. Nail matrix involvement and dermatophytomas are frequently present. Commonly the periungual and interdigital skin are affected. In this patient, the condition had been persistent for over 2 years. The patient had tried numerous prescription and OTC remedies. Pre-treatment cultures were positive for *Trichophyton metagrophytes*. Prepared was a composition as disclosed herein using 2.5% PVP-I in 99% USP Grade DMSO with no additional water or alcohols. The patient was treated by applying the solution topically twice each day to the nail itself and the surrounding skin with a nailbrush. Within one week improvement was noted in the surrounding skin infection. After 12 weeks of treatment the cultures were repeated and were found to be negative. The affected nail plate began to separate from the underlying nail bed and was removed with nail clippers. The underlying nail bed appeared to be normal and free of infection. The new nail began to grow in free of infection in above the uninfected nail bed. After 20 weeks of treatment at least 5 mm of clear nail could be seen growing free of infection.

Example 33: Paronychia; Treated with 0.5% PVP-I in 99.5% USP Grade DMSO with No Additional Water or Alcohol or Co-Solvents This patient was suffering from paronychia secondary to treatment with Epidermal Growth Factor Receptor Inhibitors for Lung Cancer. The condition often affects both finger and toenails and can be debilitating, necessitating discontinuation of the treatment regimen. It is characterized by erythematosus, painful, swollen and sometimes fluctuant proximal nails folds caused by a mixed infection involving bacteria, yeast, and fungi. Chronic inflammation of this area can lead to scarring of the nail matrix, leading to nail deformity. In this patient, the condition had been persistent for over 2 years. The patient had tried numerous prescription and OTC remedies. Pre-treatment cultures were positive for bacteria and yeast. Prepared was a composition as disclosed herein using 0.5% PVP-I in 99.5% USP Grade DMSO with no additional water or alcohols. The patient was treated by applying the solution topically twice each day to the nail itself and the surrounding skin with a nailbrush. Within one week dramatic improvement was noted in the proximal nail fold. After 4 weeks of treatment the cultures were repeated and were found to be negative. The affected nail plate began to grow in normally. After 12 weeks of treatment the proximal nail fold appeared normal without discomfort. 5 mm of new, healthy nail could be seen growing in without dystrophy.

Example 34: Paronychia; Treated with 1.0% PVP-I in 99% USP Grade DMSO with No Additional Water or Alcohol or Co-Solvents This patient was suffering from paronychia secondary to treatment with Epidermal Growth Factor Receptor Inhibitors for Lung Cancer. The condition often affects both finger and toenails and can be debilitating, necessitating discontinuation of the treatment regimen. It is characterized by erythematosus, painful, swollen and sometimes fluctuant proximal nails folds caused by a mixed infection involving bacteria, yeast, and fungi. Chronic inflammation of this area can lead to scarring of the nail matrix, leading to nail deformity. In this patient, the condition had been persistent for over 1 year. The patient had tried numerous prescription and OTC remedies. Pre-treatment cultures were positive for bacteria and yeast. Prepared was a composition as disclosed herein using 1.0% PVP-I in 99% USP Grade DMSO with no additional water or alcohols. The patient was treated by applying the solution topically twice each day to the nail itself and the surrounding skin with a nailbrush. Within one week dramatic improvement was noted in the proximal nail fold. After 4 weeks of treatment the cultures were repeated and were found to be negative. The affected nail plate began to grow in normally. After 12 weeks of treatment the proximal nail fold appeared normal without discomfort. 5 mm of new, healthy nail could be seen growing in without dystrophy.

Example 35: Paronychia; Treated with 1.5% PVP-I in 98.5% USP Grade DMSO with No Additional Water or Alcohol or Co-Solvents This patient was suffering from paronychia secondary to treatment with Epidermal Growth Factor Receptor Inhibitors for Lung Cancer. The condition often affects both finger and toenails and can be debilitating, necessitating discontinuation of the treatment regimen. It is characterized by erythematosus, painful, swollen and sometimes fluctuant proximal nails folds caused by a mixed infection involving bacteria, yeast, and fungi. Chronic inflammation of this area can lead to scarring of the nail matrix, leading to nail deformity. In this patient, the condition had been persistent for over 6 months. The patient had tried numerous prescription and OTC remedies. Pre-treatment cultures were positive for bacteria and yeast. Prepared was a composition as disclosed herein using 1.5% PVP-I in 98.5% USP Grade DMSO with no additional water or alcohols. The patient was treated by applying the solution topically twice each day to the nail itself and the surrounding skin with a nailbrush. Within one week dramatic improvement was noted in the proximal nail fold. After 4 weeks of treatment the cultures were repeated and were found to be negative. The affected nail plate began to grow in normally. After 12 weeks of treatment the proximal nail fold appeared normal without discomfort. 5 mm of new, healthy nail could be seen growing in without dystrophy.

Example 36: Paronychia; Treated with 2.0% PVP-I in 98% USP Grade DMSO with No Additional Water or Alcohol or Co-Solvents This patient was suffering from paronychia secondary to treatment with Epidermal Growth Factor Receptor Inhibitors for Lung Cancer. The condition often affects both finger and toenails and can be debilitating, necessitating discontinuation of the treatment regimen. It is characterized by erythematosus, painful, swollen and sometimes fluctuant proximal nails folds caused by a mixed infection involving bacteria, yeast, and fungi. Chronic inflammation of this area can lead to scarring of the nail matrix, leading to nail deformity. In this patient, the condition had been persistent for over 2 years. The patient had tried numerous prescription and OTC remedies. Pre-treatment cultures were positive for bacteria and yeast. Prepared was a composition as disclosed herein using 2.0% PVP-I in 99% USP Grade DMSO with no additional water or alcohols. The patient was treated by applying the solution topically twice each day to the nail itself and the surrounding skin with a nailbrush. Within one week dramatic improvement was noted in the proximal nail fold. After 4 weeks of treatment the cultures were repeated and were found to be negative. The affected nail plate began to grow in normally. After 12 weeks of treatment the proximal nail fold appeared normal without discomfort. 5 mm of new, healthy nail could be seen growing in without dystrophy.

Example 37: Paronychia; Treated with 2.5% PVP-I in 97.5% USP Grade DMSO with No Additional Water or Alcohol or Co-Solvents This patient was suffering from paronychia secondary to treatment with Epidermal Growth Factor Receptor Inhibitors for Liver Cancer. The condition often affects both finger and toenails and can be debilitating, necessitating discontinuation of the treatment regimen. It is characterized by erythematosus, painful, swollen and sometimes fluctuant proximal nails folds caused by a mixed infection involving bacteria, yeast, and fungi. Chronic inflammation of this area can lead to scarring of the nail matrix, leading to nail deformity. In this patient, the condition had been persistent for over 1 year. The patient had tried numerous prescription and OTC remedies. Pre-treatment cultures were positive for bacteria and yeast. Prepared was a composition as disclosed herein using 2.5% PVP-I in 99% USP Grade DMSO with no additional water or alcohols. The patient was treated by applying the solution topically twice each day to the nail itself and the surrounding skin with a nailbrush. Within one week dramatic improvement was noted in the proximal nail fold. After 4 weeks of treatment the cultures were repeated and were found to be negative. The affected nail plate began to grow in normally. After 12 weeks of treatment the proximal nail fold appeared normal without discomfort. 5 mm of new, healthy nail could be seen growing in without dystrophy.

Example 38: Non-Genital Verruca Vulgaris; Treated with 0.5% PVP-I in 99.5% USP Grade DMSO with No Additional Water or Alcohol or Co-Solvents This patient was suffering from non-genital verruca vulgaris (warts) of the soles of both feet. Warts in this anatomical area are extremely difficult to treat, as they often grow quite deep into the skin and have many layers of thick skin protecting them from topical treatments. The condition is often very painful with walking or running and common treatments such as Liquid Nitrogen destruction often result in significant downtime for the patient. Warts are often spread and become larger from chronic friction in the area. In this patient, the condition had been persistent for over 1 year. The patient had tried numerous prescription and OTC remedies. Prepared was a composition as disclosed herein using 0.5% PVP-I in 99% USP Grade DMSO with no additional water or alcohols. The patient was treated by applying the solution topically twice each day to the wart itself with a nailbrush. Within four weeks the warts decreased in diameter by 50%, and after 8 weeks of treatment the wart was completely resolved.

Example 39: Non-Genital Verruca Vulgaris; Treated with 1.0% PVP-I in 99% USP Grade DMSO with No Additional Water or Alcohol or Co-Solvents This patient was suffering from non-genital verruca vulgaris (warts) of the soles of both feet and hands. Warts in this anatomical area are extremely difficult to treat, as they often grow quite deep into the skin and have many layers of thick skin protecting them from topical treatments. The condition is often very painful with walking or running and common treatments such as Liquid Nitrogen destruction often result in significant downtime for the patient. The condition is also socially embarrassing for patients. Warts are often spread and become larger from chronic friction in the area. In this patient, the condition had been persistent for over 2 years. The patient had tried numerous prescription and OTC remedies. Prepared was a composition as disclosed herein using 1.0% PVP-I in 99% USP Grade DMSO with no additional water or alcohols. The patient was treated by applying the solution topically twice each day to the wart itself with a nailbrush. Within four weeks the warts decreased in diameter by 50%, and after 12 weeks of treatment the wart was completely resolved.

Example 40: Non-Genital Verruca Vulgaris; Treated with 1.5% PVP-I in 98.5% USP Grade DMSO with No Additional Water or Alcohol or Co-Solvents This patient was suffering from non-genital verruca vulgaris (warts) of the soles of both feet. Warts in this anatomical area are extremely difficult to treat, as they often grow quite deep into the skin and have many layers of thick skin protecting them from topical treatments. The condition is often very painful with walking or running and common treatments such as Liquid Nitrogen destruction often result in significant downtime for the patient. The condition is also socially embarrassing for patients. Warts are often spread and become larger from chronic friction in the area. In this patient, the condition had been persistent for over 4 years. The patient had tried numerous prescription and OTC remedies. Prepared was a composition as disclosed herein using 1.5% PVP-I in 99% USP Grade DMSO with no additional water or alcohols. The patient was treated by applying the solution topically twice each day to the wart itself with a nailbrush. Within four weeks the warts decreased in diameter by 50%, and after 8 weeks of treatment the wart was completely resolved.

Example 41: Non-Genital Verruca Vulgaris; Treated with 2.5% PVP-I in 97.5% USP Grade DMSO with No Additional Water or Alcohol or Co-Solvents This patient was suffering from non-genital verruca vulgaris (warts) of the palms of both hands. Warts in this anatomical area are extremely difficult to treat, as they often grow quite deep into the skin and have many layers of thick skin protecting them from topical treatments. The condition is often very painful with use of hands for daily tasks and common treatments such as Liquid Nitrogen destruction often result in significant downtime for the patient. The condition is also socially embarrassing for patients. Warts are often spread and become larger from chronic friction in the area. In this patient, the condition had been persistent for over 6 months. The patient had tried numerous prescription and OTC remedies. Prepared was a composition as disclosed herein using 2.5% PVP-I in 97.5% USP Grade DMSO with no additional water or alcohols. The patient was treated by applying the solution topically twice each day to the wart itself with a nailbrush. Within four weeks the warts decreased in diameter by 50%, and after 12 weeks of treatment the wart was completely resolved.

Example 42: Non-Genital Verruca Vulgaris; Treated with 3.0% PVP-I in 97% USP Grade DMSO with No Additional Water or Alcohol or Co-Solvents This patient was suffering from non-genital verruca vulgaris (warts) of knees. Warts in this anatomical area are extremely difficult to treat, as they often grow quite deep into the skin and have many layers of thick skin protecting them from topical treatments. The condition is often very painful with walking or running and common treatments such as Liquid Nitrogen destruction often result in significant downtime for the patient. The condition is also socially embarrassing for patients. Warts are often spread and become larger from chronic friction in the area. In this patient, the condition had been persistent for over 2 years. The patient had tried numerous prescription and OTC remedies. Prepared was a composition as disclosed herein using 3.0% PVP-I in 99% USP Grade DMSO with no additional water or alcohols. The patient was treated by applying the solution topically twice each day to the wart itself with a nailbrush. Within four weeks the warts decreased in diameter by 50%, and after 12 weeks of treatment the wart was completely resolved.

Example 43: Non-Genital Verruca Vulgaris; Treated with 1.0% PVP-I in 40% USP Grade DMSO with Polyethylene Glycol This patient was suffering from non-genital verruca vulgaris (warts) of the soles of both feet. Warts in this anatomical area are extremely difficult to treat, as they often grow quite deep into the skin and have many layers of thick skin protecting them from topical treatments. The condition is often very painful with walking or running and common treatments such as Liquid Nitrogen destruction often result in significant downtime for the patient. The condition is also socially embarrassing for patients. Warts are often spread and become larger from chronic friction in the area. In this patient, the condition had been persistent for over 6 months. The patient had tried numerous prescription and OTC remedies. Prepared was a composition as disclosed herein using 1.0% PVP-I in 40% USP Grade DMSO with polyethylene glycol. The patient was treated by applying the solution topically twice each day to the wart itself with a nailbrush. Within four weeks the warts decreased in diameter by 50%, and after 8 weeks of treatment the wart was completely resolved.

Example 44: Non-Genital Verruca Vulgaris; Treated with 1.5% PVP-I in 40% USP Grade DMSO with Polyethylene Glycol This patient was suffering from non-genital verruca vulgaris (warts) of the sole of one foot. Warts in this anatomical area are extremely difficult to treat, as they often grow quite deep into the skin and have many layers of thick skin protecting them from topical treatments. The condition is often very painful with walking or running and common treatments such as Liquid Nitrogen destruction often result in significant downtime for the patient. The condition is also socially embarrassing for patients. Warts are often spread and become larger from chronic friction in the area. In this patient, the condition had been persistent for over 6 months. The patient had tried numerous prescription and OTC remedies. Prepared was a composition as disclosed herein using 1.5% PVP-I in 40% USP Grade DMSO with polyethylene glycol. The patient was treated by applying the solution topically twice each day to the wart itself with a nailbrush. Within four weeks the warts decreased in diameter by 50%, and after 12 weeks of treatment the wart was completely resolved.

Example 45: Non-Genital Verruca Vulgaris; Treated with 2.0% PVP-I in 40% USP Grade DMSO with Polyethylene Glycol This patient was suffering from non-genital verruca vulgaris (warts) of the palms of both hands. Warts in this anatomical area are extremely difficult to treat, as they often grow quite deep into the skin and have many layers of thick skin protecting them from topical treatments. The condition is often very painful with daily activities and common treatments such as Liquid Nitrogen destruction often result in significant downtime for the patient. The condition is also socially embarrassing for patients. Warts are often spread and become larger from chronic friction in the area. In this patient, the condition had been persistent for over 1 year. The patient had tried numerous prescription and OTC remedies. Prepared was a composition as disclosed herein using 2.0% PVP-I in 40% USP Grade DMSO with polyethylene glycol. The patient was treated by applying the solution topically twice each day to the wart itself with a nailbrush. Within four weeks the warts decreased in diameter by 50%, and after 8 weeks of treatment the wart was completely resolved.

Example 46: Molluscum Contagiosum; Treated with 0.5% PVP-I in 99.5% USP Grade DMSO with No Additional Water or Alcohol or Co-Solvents This patient was suffering from molluscum contagiousum on the trunk. This condition is caused by a viral infection that is easily spread by touch. It affects children most commonly, but adults are not excluded. It presents as small, skin colored umbilicated papules. They can become irritated and painful. They also can become secondarily infected with bacteria. Common treatment methods can take months to work at home, or involved painful procedures for children to tolerate in the office setting. In this patient, the condition had been persistent for 3 months. The patient had tried numerous prescription and OTC remedies. Prepared was a composition as disclosed herein using 0.5% PVP-I in 99% USP Grade DMSO with no additional water or alcohols. The patient was treated by applying the solution topically twice each day to the molluscum with a nailbrush. Within 2 weeks the lesions had resolved completely.

Example 47: Molluscum Contagiosum; Treated with 1.0% PVP-I in 99% USP Grade DMSO with No Additional Water or Alcohol or Co-Solvents This patient was suffering from molluscum contagiousum on the buttocks. This condition is caused by a viral infection that is easily spread by touch. It affects children most commonly, but adults are not excluded. It presents as small, skin colored umbilicated papules. They can become irritated and painful. They also can become secondarily infected with bacteria. Common treatment methods can take months to work at home, or involved painful procedures for children to tolerate in the office setting. In this patient, the condition had been persistent for 6 months and was spreading rapidly. The patient had tried numerous prescription and OTC remedies. Prepared was a composition as disclosed herein using 1.0% PVP-I in 99% USP Grade DMSO with no additional water or alcohols. The patient was treated by applying the solution topically twice each day to the molluscum with a nailbrush. Within 2 weeks the lesions had resolved completely.

Example 48: Molluscum Contagiosum; Treated with 1.5% PVP-I in 98.5% USP Grade DMSO with No Additional Water or Alcohol or Co-Solvents This patient was suffering from molluscum contagiousum on the neck and back. This condition is caused by a viral infection that is easily spread by touch. It affects children most commonly, but adults are not excluded. It presents as small, skin colored umbilicated papules. They can become irritated and painful. They also can become secondarily infected with bacteria. Common treatment methods can take months to work at home, or involved painful procedures for children to tolerate in the office setting. In this patient, the condition had been persistent for 2 months. The patient had tried numerous prescription and OTC remedies. Prepared was a composition as disclosed herein using 1.5% PVP-I in 99% USP Grade DMSO with no additional water or alcohols. The patient was treated by applying the solution topically twice daily to the molluscum with a nailbrush. Within 2 weeks the lesions had resolved completely.

Example 49: Molluscum Contagiosum; Treated with 2.0% PVP-I in 98% USP Grade DMSO with No Additional Water or Alcohol or Co-Solvents This patient was suffering from molluscum contagiousum on the elbows and forearms. This condition is caused by a viral infection that is easily spread by touch. It affects children most commonly, but adults are not excluded. It presents as small, skin colored umbilicated papules. They can become irritated and painful. They also can become secondarily infected with bacteria. Common treatment methods can take months to work at home, or involved painful procedures for children to tolerate in the office setting. In this patient, the condition had been persistent for 5 months. The patient had tried numerous prescription and OTC remedies. Prepared was a composition as disclosed herein using 2.0% PVP-I in 99% USP Grade DMSO with no additional water or alcohols. The patient was treated by applying the solution topically twice daily to the molluscum with a nailbrush. Within 3 weeks the lesions had resolved completely.

Example 50: Gram Negative Toeweb Infection; Treated with 1.0% PVP-I in 99% USP Grade DMSO with No Additional Water or Alcohol or Co-Solvents This patient was suffering from gram-negative toe web infection. This type of infection often happens in the immunocompromised population. It presents are an eroded, macerated, erythematosus plaque in the interdigital spaces on the volar surface of the foot. It is often malodorous and painful, inhibiting the ability of the patient to walk. Gram-negative bacteria are the causative agents, and in this case the culture grew *Pseudomonas aureginosa*. In this patient, the condition had been persistent for over 2 months. The patient had tried numerous prescription and OTC remedies with temporary improvement but consistent relapses. Prepared was a composition as disclosed herein using 1.0% PVP-I in 99% USP Grade DMSO with no additional water or alcohols. The patient was treated by applying the solution topically twice each day to the infected and painful skin with a nailbrush. Within one day the pain significantly improved, and in 5 days the infection completely cleared. Cultures were negative at one week and the infection did not return.

Example 51: Gram Negative Toeweb Infection; Treated with 2.5% PVP-I in 97.5% USP Grade DMSO with No Additional Water or Alcohol or Co-Solvents This patient was suffering from gram-negative toe web infection. This type of infection often happens in the immunocompromised population. It presents are an eroded, macerated, erythematosus plaque in the interdigital spaces on the volar surface of the foot. It is often malodorous and painful, inhibiting the ability of the patient to walk. Gram-negative bacteria are the causative agents, and in this case the culture grew *Pseudomonas aeruginosa*. In this patient, the condition had been persistent for over 4 months. The patient had tried numerous prescription and OTC remedies with temporary improvement but consistent relapses. Prepared was a composition as disclosed herein using 2.5% PVP-I in 99% USP Grade DMSO with no additional water or alcohols. The patient was treated by applying the solution topically twice each day to the infected and painful skin with a nailbrush. Within three days the pain significantly improved, and in 6 days the infection completely cleared. Cultures were negative at one week and the infection did not return.

Example 52: Non-Genital Herpes Simplex Virus; Treated with 1.0% PVP-I in 40% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2 weeks. Some patients have frequent (>6) outbreaks per years. The patient had tried numerous prescription and OTC remedies but complained that none of them worked very quickly. Prepared was a composition as disclosed herein using 1.0% PVP-I in 40% USP Grade DMSO in a hydrophilic base with no additional water or alcohols. The patient was treated by applying the ointment topically twice each day to cold sore and immediately adjacent skin. Within 1 day the lesion began to shrink and pain was alleviated completely. Within 3 days the lesion was crusted over and at 5 days the lesion was completely resolved.

Example 53: Non-Genital Herpes Simplex Virus; Treated with 1.5% PVP-I in 40% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2-3 weeks. Some patients have frequent (>6) outbreaks per years. The patient had tried numerous prescription and OTC remedies but complained that none of them worked very quickly. Prepared was a composition as disclosed herein using 1.5% PVP-I in 40% USP Grade DMSO in a hydrophilic base with no additional water or alcohols. The patient was treated by applying the ointment topically twice each day to cold sore and immediately adjacent skin. Within 1 day the lesion began to shrink and pain was alleviated completely. Within 3 days the lesion was crusted over and at 7 days the lesion was completely resolved.

Example 54: Non-Genital Herpes Simplex Virus; Treated with 2.0% PVP-I in 40% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2-3 weeks. Some patients have frequent (>6) outbreaks per years. The patient had tried numerous prescription and OTC remedies but complained that none of them worked very quickly. Prepared was a composition as disclosed herein using 2.0% PVP-I in 40% USP Grade DMSO in a hydrophilic base with no additional water or alcohols. The patient was treated by applying the ointment topically twice each day to cold sore and immediately adjacent skin. Within 2 days the lesion began to shrink and pain was alleviated completely. Within 3 days the lesion was crusted over and at 6 days the lesion was completely resolved.

Example 55: Non-Genital Herpes Simplex Virus; Treated with 1.0% PVP-I in 45% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2-3 weeks. Some patients have frequent (>6) outbreaks per years. The patient had tried numerous prescription and OTC remedies but complained that none of them worked very quickly. Prepared was a composition as disclosed herein using 1.0% PVP-I in 45% USP Grade DMSO in a hydrophilic base with no additional water or alcohols. The patient was treated by applying the ointment topically twice each day to cold sore and immediately adjacent skin. Within 3 days the lesion began to shrink and pain was alleviated completely. Within 5 days the lesion was crusted over and at 7 days the lesion was completely resolved.

Example 56: Non-Genital Herpes Simplex Virus; Treated with 2.0% PVP-I in 45% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2-3 weeks. Some patients have frequent (>6) outbreaks per years. The patient had tried numerous prescription and OTC remedies but complained that none of them worked very quickly. Prepared was a composition as disclosed herein using 2.0% PVP-I in 45% USP Grade DMSO in a hydrophilic base with no additional water or alcohols. The patient was treated by applying the ointment topically twice each day to cold sore and immediately adjacent skin. Within 1 day the lesion began to shrink and pain was alleviated completely. Within 3 days the lesion was crusted over and at 6 days the lesion was completely resolved.

Example 57: Non-Genital Herpes Simplex Virus; Treated with 2.0% PVP-I in 50% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2-3 weeks. Some patients have frequent (>6) outbreaks per years. The patient had tried numerous prescription and OTC remedies but complained that none of them worked very quickly. Prepared was a composition as disclosed herein using 2.0% PVP-I in 50% USP Grade DMSO in a hydrophilic base with no additional water or alcohols. The patient was treated by applying the ointment topically twice each day to cold sore and immediately adjacent skin. Within 2 days the lesion began to shrink and pain was alleviated completely. Within 5 days the lesion was crusted over and at 8 days the lesion was completely resolved.

Example 58: Non-Genital Herpes Simplex Virus; Treated with 1.0% PVP-I in 50% USP Grade DMSO in Hydrophilic Base with No Additional Water or Alcohol or Co-Solvents This patient was suffering from non-genital herpes simplex virus (common cold sore). In this most common type of infection, after contraction via physical contact with an infected person the virus lays dormant in the dorsal root ganglia of nerves distributed in the oral area. With a precipitating stressor the inciting immunosuppression the virus replicates and causes the common cold sore. The lesions can be quite large and painful, sometimes making eating and drinking very uncomfortable. The lesions are often socially stigmatizing and cause embarrassment on the part of the patient. Cold sores are caused most commonly by Herpes Simplex Virus 1 and they last on average 2-3 weeks. Some patients have frequent (>6) outbreaks per years. The patient had tried numerous prescription and OTC remedies but complained that none of them worked very quickly. Prepared was a composition as disclosed herein using 1.0% PVP-I in 50% USP Grade DMSO in a hydrophilic base with no additional water or alcohols. The patient was treated by applying the ointment topically twice each day to cold sore and immediately adjacent skin. Within 2 days the lesion began to shrink and pain was alleviated completely. Within 4 days the lesion was crusted over and at 7 days the lesion was completely resolved.

Example 59: Post Operative Excision Sites; Treated with 1.0% PVP-I in 40% USP Grade DMSO in Hydrophilic Base with No Additional Water or Alcohol or Co-Solvents This patient had a skin cancer excised and the wound was sutured closed. This can often lead to tenderness and pain at the site, along with the risk of the procedure leaving a cosmetically unacceptable scar. Typical wound care involves cleaning the area thoroughly daily, along with applying antibiotic ointment or petrolatum in order to prevent and infection and keep the wound moist. It is well known in Dermatology that moist wound heal much better than wounds permitted to dry and crust over. Prepared was a composition as disclosed herein using 1.0% PVP-I in 40% USP Grade DMSO in a hydrophilic base with no additional water or alcohols. The patient was treated by applying the ointment topically twice daily to the wound and immediately adjacent skin. The patient denied any tenderness associated with the procedure. The wound healed very well and was quite acceptable to the patient. There was no evidence of postoperative wound infection. The patient was seen at follow-up of 6 weeks and the scar continued to heal well.

Example 60: Post Operative Excision Sites; Treated with 2.0% PVP-I in 40% USP Grade DMSO in Hydrophilic Base with No Additional Water or Alcohol or Co-Solvents This patient had a skin cancer excised and the wound was sutured closed. This can often lead to tenderness and pain at the site, along with the risk of the procedure leaving a cosmetically unacceptable scar. Typical wound care involves cleaning the area thoroughly daily, along with applying antibiotic ointment or petrolatum in order to prevent and infection and keep the wound moist. It is well known in Dermatology that moist wound heal much better than wounds permitted to dry and crust over. Prepared was a composition as disclosed herein using 2.0% PVP-I in 40% USP Grade DMSO in a hydrophilic base with no additional water or alcohols. The patient was treated by applying the ointment topically twice daily to the wound and immediately adjacent skin. The patient denied any tenderness associated with the procedure. The wound healed very well and was quite acceptable to the patient. There was no evidence of postoperative wound infection. The patient was seen at follow-up of 6 weeks and the scar continued to heal well.

Example 61: Post Operative Excision Sites; Treated with 1.0% PVP-I in 45% USP Grade DMSO in Hydrophilic Base with No Additional Water or Alcohol or Co-Solvents This patient had a skin cancer excised and the wound was sutured closed. This can often lead to tenderness and pain at the site, along with the risk of the procedure leaving a cosmetically unacceptable scar. Typical wound care involves cleaning the area thoroughly daily, along with applying antibiotic ointment or petrolatum in order to prevent and infection and keep the wound moist. It is well known in Dermatology that moist wound heal much better than wounds permitted to dry and crust over. Prepared was a composition as disclosed herein using 1.0% PVP-I in 45% USP Grade DMSO in a hydrophilic base with no additional water or alcohols. The patient was treated by applying the ointment topically twice daily to the wound and immediately adjacent skin. The patient denied any tenderness associated with the procedure. The wound healed very well and was quite acceptable to the patient. There was no evidence of postoperative wound infection. The patient was seen at follow-up of 6 weeks and the scar continued to heal well.

Example 62: Post Operative Excision Sites; Treated with 2.0% PVP-I in 40% USP Grade DMSO in Hydrophilic Base with No Additional Water or Alcohol or Co-Solvents This patient had a skin cancer excised and the wound was sutured closed. This can often lead to tenderness and pain at the site, along with the risk of the procedure leaving a cosmetically unacceptable scar. Typical wound care involves cleaning the area thoroughly daily, along with applying antibiotic ointment or petrolatum in order to prevent and infection and keep the wound moist. It is well known in Dermatology that moist wound heal much better than wounds permitted to dry and crust over. Prepared was a composition as disclosed herein using 2.0% PVP-I in 45% USP Grade DMSO in a hydrophilic base with no additional water or alcohols. The patient was treated by applying the ointment topically twice daily to the wound and immediately adjacent skin. The patient denied any tenderness associated with the procedure. The wound healed very well and was quite acceptable to the patient. There was no evidence of postoperative wound infection. The patient was seen at follow-up of 6 weeks and the scar continued to heal well.

Example 63: Post Operative Excision Sites; Treated with 1.0% PVP-I in 50% USP Grade DMSO in Hydrophilic Base with No Additional Water or Alcohol or Co-Solvents This patient had a skin cancer excised and the wound was sutured closed. This can often lead to tenderness and pain at the site, along with the risk of the procedure leaving a cosmetically unacceptable scar. Typical wound care involves cleaning the area thoroughly daily, along with applying antibiotic ointment or petrolatum in order to prevent and infection and keep the wound moist. It is well known in Dermatology that moist wound heal much better than wounds permitted to dry and crust over. Prepared was a composition as disclosed herein using 1.0% PVP-I in 50% USP Grade DMSO in a hydrophilic base with no additional water or alcohols. The patient was treated by applying the ointment topically twice daily to the wound and immediately adjacent skin. The patient denied any tenderness associated with the procedure. The wound healed very well and was quite acceptable to the patient. There was no evidence of postoperative wound infection. The patient was seen at follow-up of 6 weeks and the scar continued to heal well.

Example 64: Post Operative Excision Sites; Treated with 2.0% PVP-I in 50% USP Grade DMSO in Hydrophilic Base with No Additional Water or Alcohol or Co-Solvents This patient had a skin cancer excised and the wound was sutured closed. This can often lead to tenderness and pain at the site, along with the risk of the procedure leaving a cosmetically unacceptable scar. Typical wound care involves cleaning the area thoroughly daily, along with applying antibiotic ointment or petrolatum in order to prevent and infection and keep the wound moist. It is well known in Dermatology that moist wound heal much better than wounds permitted to dry and crust over. Prepared was a composition as disclosed herein using 2.0% PVP-I in 50% USP Grade DMSO in a hydrophilic base with no additional water or alcohols. The patient was treated by applying the ointment topically twice daily to the wound and immediately adjacent skin. The patient denied any tenderness associated with the procedure. The wound healed very well and was quite acceptable to the patient. There was no evidence of postoperative wound infection. The patient was seen at follow-up of 6 weeks and the scar continued to heal well.

Example 65: Tinea Pedis; Treated with 0.5% PVP-I in 99.5% USP Grade DMSO with No Additional Water or Alcohol or Co-Solvents This patient was suffering from tinea pedis. This common type of fungal infections involves the feet, and often accompanies onychomycosis. The skin of the interdigital web spaces becomes macerated and cracked, and often malodorous. Patients often complain of burning and itching. The entire sole of the foot may become involved. In this patient, the condition had been persistent for over 3 years. The patient had tried numerous prescription and OTC remedies. Pre-treatment cultures were positive for *Trycophyton metagrophytes*. Prepared was a composition as disclosed herein using 0.5% PVP-I in 99% USP Grade DMSO with no additional water or alcohols. The patient was treated by applying the solution topically twice each day to the involved skin with a nailbrush. Within 2 days the patient noted much improvement in the symptoms. At one week the infection was completely resolved. The patient was cultured at 2 weeks after beginning treatment and cultures were negative.

Example 66: Tinea Pedis; Treated with 1.0% PVP-I in 99% USP Grade DMSO with No Additional Water or Alcohol or Co-Solvents This patient was suffering from tinea pedis. This common type of fungal infections involves the feet, and often accompanies onychomycosis. The skin of the interdigital web spaces becomes macerated and cracked, and often malodorous. Patients often complain of burning and itching. The entire sole of the foot may become involved. In this patient, the condition had been persistent for over 2 years. The patient had tried numerous prescription and OTC remedies. Pre-treatment cultures were positive for *Trycophyton rubrum*. Prepared was a composition as disclosed herein using 1.0% PVP-I in 99% USP Grade DMSO with no additional water or alcohols. The patient was treated by applying the solution topically twice each day to the involved skin with a nailbrush. Within 3 days the patient noted much improvement in the symptoms. At one week the infection was completely resolved. The patient was cultured at 2 weeks after beginning treatment and cultures were negative.

Example 67: Tinea Pedis; Treated with 1.5% PVP-I in 98.5% USP Grade DMSO with No Additional Water or Alcohol or Co-Solvents This patient was suffering from tinea pedis. This common type of fungal infections involves the feet, and often accompanies onychomycosis. The skin of the interdigital web spaces becomes macerated and cracked, and often malodorous. Patients often complain of burning and itching. The entire sole of the foot may become involved. In this patient, the condition had been persistent for over 10 years. The patient had tried numerous prescription and OTC remedies. Pre-treatment cultures were positive for *Trycophyton metagrophytes*. Prepared was a composition as disclosed herein using 1.5% PVP-I in 98.5% USP Grade DMSO with no additional water or alcohols. The patient was treated by applying the solution topically twice each day to the involved skin with a nailbrush. Within 6 days the patient noted much improvement in the symptoms. At 2 weeks the infection was completely resolved. The patient was cultured at 2 weeks after beginning treatment and cultures were negative.

Example 68: Tinea Pedis; Treated with 2.0% PVP-I in 98% USP Grade DMSO with No Additional Water or Alcohol or Co-Solvents This patient was suffering from tinca pedis. This common type of fungal infections involves the feet, and often accompanies onychomycosis. The skin of the interdigital web spaces becomes macerated and cracked, and often malodorous. Patients often complain of burning and itching. The entire sole of the foot may become involved. In this patient, the condition had been persistent for over 5 years. The patient had tried numerous prescription and OTC remedies. Pre-treatment cultures were positive for *Trycophyton metagrophytes*. Prepared was a composition as disclosed herein using 2.0% PVP-I in 98% USP Grade DMSO with no additional water or alcohols. The patient was treated by applying the solution topically twice each day to the involved skin with a nailbrush. Within 2 days the patient noted much improvement in the symptoms. At 10 days the infection was completely resolved. The patient was cultured at 2 weeks after beginning treatment and cultures were negative.

Example 69: Tinea Pedis; Treated with 10.0% PVP-I in 99% USP Grade DMSO with No Additional Water or Alcohol or Co-Solvents This patient was suffering from tinea pedis. This common type of fungal infections involves the feet, and often accompanies onychomycosis. The skin of the interdigital web spaces becomes macerated and cracked, and often malodorous. Patients often complain of burning and itching. The entire sole of the foot may become involved. In this patient, the condition had been persistent for over 6 years. The patient had tried numerous prescription and OTC remedies. Pre-treatment cultures were positive for *Trycophyton metagrophytes*. Prepared was a composition as disclosed herein using 10.0% PVP-I in 99% USP Grade DMSO with no additional water or alcohols. The patient was treated by applying the solution topically twice each day to the involved skin with a nailbrush. Within 4 days the patient noted much improvement in the symptoms. At 8 days the infection was completely resolved. The patient was cultured at 2 weeks after beginning treatment and cultures were negative.

Example 70: Psoriatic Nail Disease; Treated with 1.0% PVP-I in 99% USP Grade DMSO with No Additional Water or Alcohol or Co-Solvents This patient was suffering from psoriasis involving the nails. Psoriasis is common inflammatory condition that can affect the skin, nails, and joints. When nail involvement is present, it can be debilitating for the patient. It can involve finger and toenails and can become quite painful. It is also socially stigmatizing as nails can become completely disfigured. Within the nail unit itself, psoriasis can affect the matrix, nail bed or nail plate. It clinically can present as total nail dystrophy, pitting or ridging of the nails. In this patient, the condition had been persistent for over 3 years. The patient had tried numerous prescription and OTC remedies. Prepared was a composition as disclosed herein using 1.0% PVP-I in 99% USP Grade DMSO with no additional water or alcohols. The patient was treated by applying the solution topically twice each day to the involved nail and proximal nail fold. Within 4 weeks the patient noted healthy, normal appearing nail growing in from the base of the nail. At 12 weeks, she demonstrated 5 mm of normal growth from the base. She continues with therapy to date and continues to maintain clear nails.

Example 71: Psoriatic Nail Disease; Treated with 2.0% PVP-I in 98% USP Grade DMSO with No Additional Water or Alcohol or Co-Solvents This patient was suffering from psoriasis involving the nails. Psoriasis is common inflammatory condition that can affect the skin, nails, and joints. When nail involvement is present, it can be debilitating for the patient. It can involve finger and toenails and can become quite painful. It is also socially stigmatizing as nails can become completely disfigured. Within the nail unit itself, psoriasis can affect the matrix, nail bed or nail plate. It clinically can present as total nail dystrophy, pitting or ridging of the nails. In this patient, the condition had been persistent for over 12 years. The patient had tried numerous prescription and OTC remedies. Prepared was a composition as disclosed herein using 2.0% PVP-I in 98% USP Grade DMSO with no additional water or alcohols. The patient was treated by applying the solution topically twice each day to the involved nail and proximal nail fold. Within 6 weeks the patient noted healthy, normal appearing nail growing in from the base of the nail. At 12 weeks, he demonstrated 5 mm of normal growth from the base. He continues with therapy to date and continues to maintain clear nails.

Example 72: Psoriatic Nail Disease; Treated with 0.5% PVP-I in 99.5% USP Grade DMSO with No Additional Water or Alcohol or Co-Solvents This patient was suffering from psoriasis involving the nails. Psoriasis is common inflammatory condition that can affect the skin, nails, and joints. When nail involvement is present, it can be debilitating for the patient. It can involve finger and toenails and can become quite painful. It is also socially stigmatizing as nails can become completely disfigured. Within the nail unit itself, psoriasis can affect the matrix, nail bed or nail plate. It clinically can present as total nail dystrophy, pitting or ridging of the nails. In this patient, the condition had been persistent for over 5 years. The patient had tried numerous prescription and OTC remedies. Prepared was a composition as disclosed herein using 0.5% PVP-I in 99.5% USP Grade DMSO with no additional water or alcohols. The patient was treated by applying the solution topically twice each day to the involved nail and proximal nail fold. Within 4 weeks the patient noted healthy, normal appearing nail growing in from the base of the nail. At 12 weeks, she demonstrated 5 mm of normal growth from the base. She continues with therapy to date and continues to maintain clear nails.

Example 73: Effect of Anhydrous 1% PVP-I for Treatment of Onychomycosis

Thirteen patients with fungal culture-positive onychomycosis presented to the practice at the Bryn Mawr Skin and Cancer Institute over a 3-month period and were prescribed topical PVP-I, 1% anhydrous solution in DMSO, as clinically indicated. Patients applied the solution twice daily to the affected nail folds, subungual space and nail plate for 12 weeks. Responses were recorded by clinical examination findings, patient-reported symptoms and fungal culture (Mycosel™ agar) results.

Five (5) men and eight (8) women with a median age of 57 (range 31-71) were evaluated. Patient demographic, clinical and mycological data are detailed in Table 1.

| Patient | Age | Gender | Previous Treatment | Culture Week 0/12 | Discoloration Pre/Post | Pain Pre/Post | Burning Pre/Post | Itch Pre/Post |
|---|---|---|---|---|---|---|---|---|
| 01* | 53 | F | Laser, Lamisil, OTC | +/+ | 5/4 | 0/0 | 0/0 | 0/0 |
| 02 | 49 | F | OTC | +/− | 3/2 | 1/1 | 0/0 | 1/0 |
| 03 | 47 | F | None | +/− | 4/3 | 1/0 | 1/0 | 1/1 |
| 04 | 71 | F | OTC | +/− | 4/2 | 0/0 | 0/0 | 1/1 |
| 05 | 62 | F | None | +/− | 4/3 | 2/1 | 2/1 | 2/0 |
| 06 | 36 | F | Rx Lacquer | +/− | 5/4 | 0/0 | 0/0 | 1/0 |
| 07* | 67 | F | Lamisil, OTC | +/− | 5/3 | 3/1 | 0/0 | 2/1 |
| 08 | 57 | M | OTC | +/− | 3/1 | 0/0 | 0/0 | 2/1 |
| 09 | 60 | F | Rx Lacquer | +/− | 4/2 | 0/0 | 0/0 | 0/0 |
| 10* | 65 | M | Lamisil, Rx Lacquer | +/+ | 5/3 | 4/0 | 3/1 | 3/0 |
| 11* | 67 | M | Lamisil, Rx Lacquer | +/− | 4/1 | 1/0 | 0/0 | 0/0 |
| 12 | 33 | M | OTC | +/− | 1/0 | 0/0 | 0/0 | 0/0 |
| 13 | 31 | M | None | +/− | 4/2 | 0/0 | 0/0 | 1/0 |

*Indicates the presence of dermatophytoma (mass of fungal hyphae present within the nail represented by a thick yellow streak in the nail).

For the numerial scores above, patients were asked to assign a numerical value for each of the subjective categories listed in the table, with 0 indicating complete lack of the symptoms and 5 indicating severe involvement. For Discoloration, patients graded the color of nail with the following point scale: 0—clear, 1—white, 2—yellow/white, 3—yellow, 4—green, 5—green/black.

Ten (10) out of thirteen (13) had prior topical and/or oral treatments (range=1-3; median=1). At 12 weeks, 11/13 patients (85%) had negative fungal cultures (compared to positive baseline cultures) and all demonstrated clinical improvement as assessed by nail discoloration (Figure 1 and Table 1). The 2 patients with positive fungal cultures at 12 weeks were 2/4 patients (Table 1—#1, 7, 10, 11) to have had clinically severe infections including dermatophytoma (mass of fungal hyphae within the nail plate represented by a thick yellow streak). Of the 10/13 patients who reported pre-treatment symptoms (pain, burning, pruritus), all 10 (100%) reported symptom improvement by 12 weeks (Table 1). No patients discontinued use of PVP-I 1% anhydrous solution due to intolerance and there were no reported adverse reactions.

It is shown here for the first time that treatment with this well-tolerated formulation of topical PVP-I, 1% anhydrous solution in DMSO, appears to eradicate fungal organisms from within the nail itself, rendering it an effective treatment for onychomycosis and suggesting potential benefit in paronychia. The preliminary results of this case series appears to address the above issue of nail plate reinfection. All 13 patients demonstrated positive fungal cultures prior to initiation of treatment and at 12 weeks, 11/13 patients (85%) had negative culture results. Four (4) patients manifested dermatophytomas. This nail sign identifies a recalcitrant subset since current therapies do not effectively access the fungal hyphae masses occupying the nail plate. Of note, 2/4 patients (50%) with dermatophytomas converted to negative fungal cultures at 12 weeks which suggests that the PVP-I 1% anhydrous solution has the potential ability to rapidly penetrate and eradicate fungal foci in nails. Though the current study did not directly assess the treatment effect on *Pseudomonas*, the results support an efficacy in this common co-morbid infection as well.

Example 74: Mature Hypertrophic Scars; Treated with 1.0% PVP-I in 40% USP Grade DMSO in Hydrophilic Base with No Additional Water or Alcohol or Co-Solvents This patient had a 6 month-old scar after a C-Section procedure was performed and the wound was stapled closed. This procedure often leads to an elevated, firm pink cosmetically unacceptable scar that can be tender or pruritic. Certain areas of the body are much more prone to developing hypertrophic scars, and the lower abdomen is one of those sites. It is well known in Dermatology that hypertrophic scars are very difficult to treat and tend to be recalcitrant to treatment. Injections with steroids are potential treatment options, but do not come without risk. Much research has been dedicated to studying the pathophysiology behind scar formation, but still little is understood at this point. A formulation of 1.0% PVP-I in 40% USP Grade DMSO in a hydrophilic base with no additional water or alcohols was prepared. The patient was treated by applying the formulation topically twice daily to the hypertrophic scar. The patient denied any tenderness or irruption associated with the procedure. The patient was seen at 6 weeks and 10 weeks after beginning use, and noted significant decrease in the pruritus. The appearance of the scar, softened and flattened, and the erythematosus color of the skin faded.

Example 75: Mature Hypertrophic Scars; Treated with 1.0% PVP-I in 30% USP Grade DMSO in Hydrophilic Base with No Additional Water or Alcohol or Co-Solvents This patient had a 5 month-old scar after a Mohs procedure was performed and the wound was sutured closed via a transposition flap. This procedure can lead to an elevated, firm pink cosmetically unacceptable scar that can be tender or pruritic. Certain areas of the body are much more prone to developing hypertrophic scars, and the nasofacial junction is one of those sites. It is well known in Dermatology that hypertrophic scars are very difficult to treat and tend to be recalcitrant to treatment. Injections with steroids are potential treatment options, but do not come without risk. Much research has been dedicated to studying the pathophysiology behind scar formation, but still little is understood at this point. A formulation of 01.0% PVP-I in 30% USP Grade DMSO in a hydrophilic base with no additional water or alcohols was prepared. The patient was treated by applying the formulation topically twice daily to the hypertrophic scar. The patient denied any tenderness or irruption associated with the procedure. The patient was seen at the 4 weeks and 8 weeks after beginning use, and noted significant decrease in the pruritus. The scar softened and flattened, and the erythematosus color of the skin faded.

Example 76: Mature Hypertrophic Scars; Treated with 1.5% PVP-I in 40% USP Grade DMSO in Hydrophilic Base with No Additional Water or Alcohol or Co-Solvents This patient had a 3 month-old scar after a cosmetic procedure was performed for the removal of benign melanocytic nevi on the face and the wounds were sutured closed. This procedure can lead to an elevated, firm pink cosmetically unacceptable scar that can be tender or pruritic. Certain areas of the body are much more prone to developing hypertrophic scars, and the forehead and check are amongst those sites. It is well known in Dermatology that hypertrophic scars are very difficult to treat and tend to be recalcitrant to treatment. Injections with steroids and laser therapy are potential treatment options, but do not come without risk. Much research has been dedicated to studying the pathophysiology behind scar formation, but still little is understood at this point. A formulation of 1.5% PVP-I in 40% USP Grade DMSO in a hydrophilic base with no additional water or alcohols was prepared. The patient was treated by applying the formulation topically twice daily to the hypertrophic scar. The patient denied any tenderness or irruption associated with the procedure. The patient was seen at the 4 weeks and 10 weeks after beginning use, and noted significant decrease in the pruritus. The scar softened and flattened, and the erythematosus color of the skin faded.

Example 77: Mature Keloid Scar; Treated with 1.0% PVP-I in 40% USP GRADE DMSO in Hydrophilic Base with No Additional Water or Alcohol or Co-Solvents This patient had a 3 month-old scar after a wide excision was performed to remove a Malignant Melanoma and the wound was sutured closed. This procedure can lead to an elevated, firm pink cosmetically unacceptable scar that can be tender or pruritic. Certain areas of the body are much more prone to developing hypertrophic scars, and the back is a very common site. It is well known in Dermatology that keloid scars are very difficult to treat and tend to be recalcitrant to treatment. Injections with steroids and laser therapy are potential treatment options, but do not come without risk. Much research has been dedicated to studying the pathophysiology behind scar formation, but still little is understood at this point. A formulation of 1.0% PVP-I in 40% USP Grade DMSO in a hydrophilic base with no additional water or alcohols was prepared. The patient was treated by applying the formulation topically twice daily to the keloid scar. The patient denied any tenderness or irruption associated with the procedure. The patient was seen at the 4 weeks, 8 weeks, and 12 weeks after beginning use, and noted significant decrease in the pruritus. The scar softened and flattened, and the erythematosus color of the skin faded.

Example 78: Mature Keloid Scar; Treated with 1.0% PVP-I in 50% USP GRADE DMSO in Hydrophilic Base with No Additional Water or Alcohol or Co-Solvents This patient had a 7 month-old scar after a wide excision was performed to remove a Malignant Melanoma and the wound was sutured closed. This procedure can lead to an elevated, firm pink cosmetically unacceptable scar that can be tender or pruritic. Certain areas of the body are much more prone to developing hypertrophic scars, and the upper arm is one of these sites. It is well known in Dermatology that keloid scars are very difficult to treat and tend to be recalcitrant to treatment. Injections with steroids and laser therapy are potential treatment options, but do not come without risk. Much research has been dedicated to studying the pathophysiology behind scar formation, but still little is understood at this point. A formulation of 1.0% PVP-I in 50% USP Grade DMSO in a hydrophilic base with no additional water or alcohols was prepared. The patient was treated by applying the formulation topically twice daily to the keloid scar. The patient denied any tenderness or irruption associated with the procedure. The patient was seen at the 4 weeks, 8 weeks, and 16 weeks after beginning use, and noted significant decrease in the pruritus. The scar softened and flattened, and the erythematosus color of the skin faded.

Example 79: Lichen Planus Nail Disease; Treated with 1.0% PVP-I in 99% USP Grade DMSO with No Additional Water or Alcohol or Co-Solvents This patient was suffering from Lichen Planus involving the nails. Lichen Planus is an uncommon condition that can affect the skin, mucosal membranes, hand and nails. Nail involvement is rare, but can be debilitating. The condition affects the nail matrix, leading to dorsal pteryigium of the nail, along with severe scarring, chronic nail shedding and pain from affected nail folds. It can involve finger and toenails and can become quite painful. It is also socially stigmatizing as nails can become completely disfigured. In this patient, the condition had been persistent for over 10 years. The patient had seen 10 Dermatologists that failed to correctly identify the condition. She had tried numerous prescription and OTC remedies. A formulation of 1.0% PVP-I in 99% USP Grade DMSO with no additional water or alcohols was prepared. The patient was treated by applying the formulation topically twice each day to the involved nail and proximal nail fold. Within 4 weeks the patient noted the inflammation associated with the nail matrix had greatly subsided and the pain had significantly improved. At 8 weeks she noted new, normal appearing nails growing in several of her fingernails. At 12 weeks, 2 of her nails were clear and returning to a normal appearing nail.

Example 80: Arthropod Assault; Treated with 1.0% PVP-I in 99% USP GRADE DMSO with No Additional Water or Alcohol or Co-Solvents This patient was suffering numerous arthropod assaults, more commonly known as bug bites. Numerous species of insects bite the skin, ranging from mosquitos to bees and flies. This is a common occurrence and often results in extremely pruritic raised erythematosus papules and plaques. Depending upon an individuals' unique response to a bite, the reaction can last anywhere from a few minutes to weeks. A formulation of 1.0% PVP-I in 99% USP Grade DMSO with no additional water or alcohols was prepared. The patient applied the formulation immediately after recognizing the bite as being pruritic. The symptoms of itching and the lesion that typically followed was completely eliminated and no further application was needed.

Example 81: Arthropod Assault; Treated with 0.5% PVP-I in 99.5% USP GRADE DMSO with No Additional Water or Alcohol or Co-Solvents This patient was suffering numerous arthropod assaults, more commonly known as bug bites. Numerous species of insects bite the skin, ranging from mosquitos to bees and flies. This is a common occurrence and often results in extremely pruritic raised erythematosus papules and plaques. Depending upon an individuals' unique response to a bite, the reaction and lesions that ensue can last anywhere from a few minutes to weeks. A formulation of 0.5% PVP-I in 99.5% USP Grade DMSO with no additional water or alcohols was prepared. The patient applied the formulation the day following the bites after the lesion had appeared. She utilized the formulation a total of 3 times with complete disappearance of the lesions within one day.

It will be appreciated by those skilled in the art that changes could be made to the exemplary embodiments shown and described above without departing from the broad inventive concept thereof. It is understood, therefore, that the disclosure herein is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. A method for treating a skin disease complicated by microbial colonization or infection, said method comprising:
    (a) providing a pharmaceutically acceptable composition comprising
        0.1% to 10% (w/w) of a therapeutic agent which is povidone-iodine (PVP-I) wherein the 0.1% to 10% PVP-I is dissolved in
        greater than 33% (w/w) DMSO and at least one co-solvent;
        and a pharmaceutically acceptable carrier which is a gel to form a gel composition; and
    (b) topically administering the composition to a patient in need of treatment of the skin disease, wherein the skin disease is molluscum contagiosum.

* * * * *